US007078167B2

(12) United States Patent
Delenstarr et al.

(10) Patent No.: US 7,078,167 B2
(45) Date of Patent: Jul. 18, 2006

(54) ARRAYS HAVING BACKGROUND FEATURES AND METHODS FOR USING THE SAME

(75) Inventors: Glenda C. Delenstarr, Belmont, CA (US); Paul K. Wolber, Los Altos, CA (US); Theodore R. Sana, Santa Clara, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 2 days.

(21) Appl. No.: 09/899,381

(22) Filed: Jul. 2, 2001

(65) Prior Publication Data

US 2002/0068293 A1   Jun. 6, 2002

Related U.S. Application Data

(63) Continuation-in-part of application No. 09/398,399, filed on Sep. 17, 1999.

(51) Int. Cl.
*C12Q 1/68* (2006.01)
*G01N 33/00* (2006.01)
*C07H 21/02* (2006.01)
*C07H 21/04* (2006.01)

(52) U.S. Cl. .................. 435/6; 436/94; 536/23.1; 536/24.3

(58) Field of Classification Search .............. 435/6, 435/91.1, 91.2, 287.2, 810; 436/94, 800, 436/805; 536/23.1, 24.31, 24.33
See application file for complete search history.

(56) References Cited

U.S. PATENT DOCUMENTS

| 4,868,105 | A |   | 9/1989  | Urdea et al. |
| 5,124,246 | A |   | 6/1992  | Urdea et al. |
| 5,143,854 | A |   | 9/1992  | Pirrung et al. |
| 5,200,313 | A | * | 4/1993  | Carrico ........................... 435/6 |
| 5,445,934 | A | * | 8/1995  | Fodor et al. .................... 435/6 |
| 5,563,034 | A | * | 10/1996 | Brink et al. .................... 435/6 |
| 5,681,702 | A |   | 10/1997 | Collins et al. |
| 5,723,320 | A | * | 3/1998  | Dehlinger .................. 435/91.1 |
| 5,807,522 | A |   | 9/1998  | Brown et al. |
| 6,077,673 | A | * | 6/2000  | Chenchik et al. ............... 435/6 |
| 6,077,674 | A | * | 6/2000  | Schleifer et al. ............... 435/6 |
| 6,110,426 | A |   | 8/2000  | Shalon et al. |
| 2003/0113724 | A1 | * | 6/2003 | Schembri et al. .............. 435/6 |

FOREIGN PATENT DOCUMENTS

JP          07147982         6/1995

(Continued)

OTHER PUBLICATIONS

CAS Registry No. 240395-56-6 (sequence printout).*

(Continued)

*Primary Examiner*—Bradley L. Sisson

(57) ABSTRACT

Nucleic acid arrays that have background features, and methods for using the same, are provided. The subject nucleic acid arrays include both hybridization features and background features, where the background features provide a background signal in a hybridization assay that is made up of a feature substrate component, a nucleic acid probe component and a nucleic acid probe non-specific binding component. In practicing the subject methods, the arrays are contacted with a sample and signals are observed for both hybridization features and background features. The background feature signal is then subtracted from the hybridization feature signal to obtain a background corrected hybridization feature signal that is employed as the output of the assay, e.g., to determine the presence, either qualitatively or quantitatively, of the analyte target nucleic acid in the sample. Also provided are kits for use in practicing the subject methods.

16 Claims, 13 Drawing Sheets

FOREIGN PATENT DOCUMENTS

| WO | WO 89/10977 | 11/1989 |
|---|---|---|
| WO | WO 95/21944 | 2/1994 |
| WO | WO95/35505 | 6/1995 |
| WO | WO 98/24933 | 6/1998 |

OTHER PUBLICATIONS

Blanchard et al., "High—density oligonucleotide arrays, " Biosensors & Bioelectonics, 1996, vol. 11. no. 6/7, pp. 687/690.*

Iitia et al., Biotechniques, 1994, vol. 17 pp. 566-573.*

Chen, Y et al. "Ratio-Based Decisions and the Quantitative Analysis of cDNA Microarry Images", Journal of Biomedical Optics, vol.2, No. 4, pp. 364-374 (1994).

DeRisi, J.I. et al., "Exploring the Metabolic and Genetic Control of the Gene Expression on a Genetic Scale", Science, vol. 278, pp. 680-686 (1997).

Wetmur, J.G. "DNA Probes: Applications of the Principals of Nucleic Acid Hybridization", Critical Reviews in Biochemistry and Molecular Biology, vol. 26. No. 3/4, pp. 227-259 (1991).

Blanchard et al. "High Densityoligonucleotide array" Biosensors and Bioelectrics, vol., No. 6/7. pp. 687-690, Apr. 1996.

Becker-Andre et al. Absolute mRNA Qualification using the polymerase chain reaction (PCR). Anovel approach by a PCR aided transcript titration assay (PATTY) Nucleic Acids Research, vol. 17, No. 221989.

Southern et al. "Analyzing and Comparing Nucleic Acid Sequences By Hybridization to Arrays of Oligonucleotides: Evaluation Using Experimental . . . "Genomics 13, 1008-1017 (1992).

Lennon et al. "Hybridization analyses of arrayed cDNA libraries" Trends in Genetics, Oct. 1991 vol. 7, No. 10 pp. 314-317.

Becker- Andre et al. "Absolute Levels of mRNA by Polymerase Chain Reaction—Aided Transcript Titration Assay"Methods in Enzymology, vol. 218, pp. 420-445.

Zhao et al. "High—density cDNA filter analysis: a novel approach for large-scale, quantitative analysis of gene expression"Gene, 156 (1995) 207-213.

Kerfof et al. "A procedure for making simultaneous determinations of the relative levels of gene transcripts in tissues or cells"Analytical Biochemistry, 188, 349-355 (1990).

Ronald Rosenburg, Globe Staff, The Boston Globe, Nov. 30 1994, City Edition, Section: Economy, p. 45 "Firms in Biochip; Genetics Institute, Affymetrix in Joint Quest for new drugs".

Lipshutz et al. "Using Oligonucleotide Probe Arrays to Access Genetic Diversity" BioFeature vol. 19, No. 3 (1995), pp. 442-447.

Strezoska et al. "DNA sequencing byb hybridization: 100 bases read by a non-gel-based method" Proc. Natl. Acad. Sci. USA, vol. 88, pp. 10089-10093, Nov. 1991.

Pease et al. Light—generated Oligonucleotide arrays for rapid DNA sequence analysis Proc. Natl. Acad. Sci USA, Col. 91. pp. 5022-5026, May 1994.

Ravaggi et al. "Quantification of Hepatitis C Virus RNA by Competitive Amplification of RNA from Denatured Serum and Hybridization on Microtiter Plates" Journal of Clinical Microbiology, Feb. 1995, p. 265-269.

Hahn et al. "Quantitative Polymerase Chain Reaction with Enzyme—Linked Immunosorbent Assay Detection of Selectively Digested Amplified Sample and COntrol DNA"Analytical Biochemistry, 229: 236-248 (1995).

Jalava et al. "Quantification of Hepatitis B Virus DNA by Competitive Amplification and Hybridization of Microplates"BioTechniques, vol. 15. NO 1 (1993) pp. 134-139.

Bhatia et al. Comparison of Glyceraldehyde-3-phosphate Dehydrogenase and 28S-Ribosomal RNA Gene Expression as RNA Loading Controls for Northern Blot Analysis of Cell Lines of Varying Malignant Potential Anlaytical Biochemistry 216, 223-226 (1994).

Chalifour et al. "A method for Analysis of Gene expression Patterns"Analytical Biochemistry 216, 299-304 (1994).

DuBois et al. "Molar Quantification of Specific Messanger Ribonucleic Acid Expression in Northern Hybridization Using cRNA Standards"Analytical Biochemistry 210, 140-1444 (1993).

Ferre-Aubineau et al. "Colorimetric microtiter plate hybridization assay using monoclonal antibody for detection of an amplified human immunodeficiency virus target"Journal of Virological Methods, 55 (1995) 145-151.

Henderson et al. "A Reliable Method for Northern Blot Analysis Using Synthetic Oligonucleotide Probes" Biotechniques, vol. 10, No. 2 (1991) pp. 190-197.

Ogretman et al. "Internal cRNA Standards for Quantitative Northern Analysis"BioTechniques, vol. 14, No. 6 (1993) pp. 935-941.

Kawai et al. "A simple method of HLA-DRB typing using enzymatically amplified DNA and immobilized probes on microtiter plate" Human Immunology, 41, 121-126 (1994).

Nakamori et al. "A simpe and useful method for simultaneous screening of elevated leves of expression of a variety of oncogenes in malignant cells" Jpn. J. Cancer Res. (Gann), 79. 1311-1317, Dec. 1988.

Kohsaka et al. "Microtiter format gene quantification by covalent capture of competitive PCR products: application to HIV-1 detection" Nucleic Acids Research, 1993, vol. 21, No. 15 3469-3472 1993 Oxford University Press.

Taniguchi et al. "Competitive RT-PCR ELISA: a rapid, sensitive and non-radioactive method to quantitate cytokine mRNA"Journal of Immunological Methods 169 (1994) 101-109.

Olney et al. "A quantitative assay for IGF-I and IGF binding protein mRNAs expression in malignant melanoma cells" Molecular and Cellular Endocrinology 110 (1995) 213-223.

Richard J. Wilkins, "Allele-specific oligonucleotide probes for mRNA" BioTechniques, vol. 14, No. 3 (1993) pp. 352-354.

Jessen-Eller et al. "Quantitation of Metallothionein mRNA by RT-PCR and Chemiluminesence" Biotechniques, vol. 17. No. 4 (1994).

Apostolakos et al. "Measurement of gene expression by multiplex competitve polymerase chain reaction" Analytical Biochemistry 213, 277-284 (1993).

Thompson et al. "Current concepts in quantitative molecular hybridization" Clin Biochem. vol 23, pp. 261 - 266 (1990).

Wallace et al. "Hybridization of synthetic oligodeoxyribonucleotides to x 174 DNA: the effect of single base pair mismatch" Nucleic Acids Research vol. 6., No. 11 1979, pp. 3543-3557.

Kaczmarek et al. "Expression of cell-cycle-dependent genes in phytohohemagglutinin-stimulated human lymphocytes" Proc. Natl. acad. Sci USA, vol. 82, pp. 5375-5379, Aug. 1985 Cell Biology.

Eggers et al. "A microchip for quantitative detection of molecules utilizing luminescent and radioisotope reporter groups" Biotechniques, vol. 17, no. 3 (1994) pp. 516-254.

Iitia et al. "Detection of a point mutation using short oligonucleotide probes in allele—specific hybridization" Biotechniques, vol. 17, No. 3 (1994) pp. 566-573.

Liang et al. "Differential display of eukaryotic messenger RNA by means of the polymerase chain reaction" Science, vol. 257, Aug. 14, 1992 pp. 967-971.

Kolls et al. "cDNA Equalization for Reverse Transcription—Polymerase Chain Reaction Quantitation"Analytical Biochemistry, 208, 264-269 (1993).

Molecular Cloning —A laboratory manuel, second edition, Cold Spring Harbor Laboratory Press 1989" Synthetic Oligonucleotide Probes".

Kawasaki et al. "Genetic analysis using polymerase chain reaction-amplified DNA and immobilized oligonucleotide probes: reverse dot-blot typing" Methods in Enzymology, vol. 218 pp. 369-381.

Scheuerman et al. "Polymerase chain reaction-based mRNA quantification using and internal standard: analysis of oncogene expression" Methods Enzymmol. 1993: 218: 446-73.

Maskos et al. "A novel method for the parallel analysis of multiple mutations in multiple samples"Nucleic Acids Research, 1993, vol. 21, No. 9. pp. 2269-2270.

Mirzabekov et al. "DNA sequencing by hybridization —a megasequencing method and a diagnostic tool?" 1994, Elsevier Science Ltd. Reviews pp. 27-32.

Day et al. "Electrophoresis for genotyping: temporal thermal gradiant gel electrophoresis for profiling of oligonucleotide dissociation" Nucleic Acids Research; 1995, vol. 23. No. 13, pp. 2404-2412.

* cited by examiner

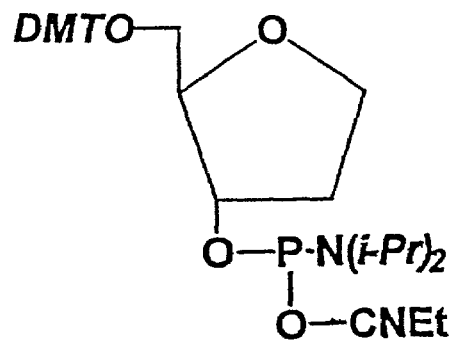
*I: 5'-O-Dimethoxytrityl-1',2'-Dideoxyribose-3'-
[(2-cyanoethyl)-(N,N-diisopropyl)]-phosphoramidite*
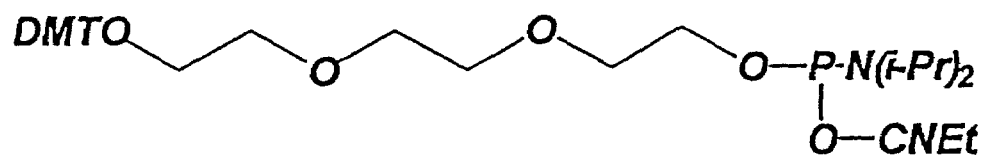
*II: 9'-O-Dimethoxytrityl-triethyleneglycol,
1-[(2-cyanoethyl)-(N,N-diisopropyl)]-phosphoramidite*
FIG. 5

SEQUENCE LISTING

<160> NUMBER OF SEQ ID NOS: 53

<210> SEQ ID NO 1
<211> LENGTH: 983
<212> TYPE: RNA
<213> ORGANISM: homo sapiens
<220> FEATURE:
<223> OTHER INFORMATION: synthetically generated cRNA

<400> SEQUENCE: 1

| | | | | | |
|---|---|---|---|---|---|
| gcaugugggc | caugaggucc | accacccugu | ugcuguagcc | aaauucguug | ucauaccagg | 60 |
| aaaugagcuu | gacaaagugg | ucguugaggg | caaugccagc | cccagcguca | aaggguggagg | 120 |
| agugggguguc | gcuguugaag | ucagaggaga | ccaccuggug | cucaguguag | cccaggaugc | 180 |
| cuuugagggg | gcccuccgac | gccugcuuca | ccaccuucuu | gaugucauca | uauuuggcag | 240 |
| guuuuucuag | acggcaagguc | agguccacca | cugacacguu | ggcaguggggg | acacggaagg | 300 |
| ccaugccagu | gagcuucccg | ucuagcucag | ggaugaccuu | gcccacagcc | uuggcagcgc | 360 |
| caguagaggc | agggaugaug | uucuggagag | ccccgcggcc | aucacgccac | aguuucccgg | 420 |
| aggggccauc | cacagucuuc | uggguggcag | ugauggcaug | gacuguugguc | augaguccuu | 480 |
| ccacgauacc | aaaguuguca | uggaugaccu | uggccagggg | ugcuaagcag | uuggugguc | 540 |
| aggaggcauu | gcugaugauc | uugaggcugu | ugucauacuu | cucauggguuc | acacccauga | 600 |
| cgaacauggg | ggcaucagca | gaggggggcag | agaugaugac | ccuuuuggcu | cccccccugca | 660 |
| aaugagcccc | agccuucucc | auggugguga | agacgccagu | ggacuccacg | acguacucag | 720 |
| cgccagcauc | gccccacuug | auuuuggagg | gaucucgcuc | cuggaagaug | gugauggggau | 780 |
| uuccauugau | gacaagcuuc | ccguucucag | ccuugacggu | gccauggaau | uugccauggg | 840 |
| uggaaucaua | uuggaacaug | uaaaccaugu | aguugagguc | aauugaaggggg | ucauugaugg | 900 |
| caacaauauc | cacuuuacca | gaguuaaaag | cagcccuggu | gaccaggcgc | ccaauacgac | 960 |
| caaauccguu | gacuccgacc | uuc | | | | 983 |

<210> SEQ ID NO 2
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 2
atcatcgtag ctggtcagtg tatcc     25

<210> SEQ ID NO 3
<211> LENGTH: 25
<212> TYPE: DNA
<213> ORGANISM: Artificial Sequence
<220> FEATURE:
<223> OTHER INFORMATION: synthetic oligonucleotide

```
<400> SEQUENCE: 3
ggatacactg accagctacg atgat                                           25

<210> SEQ ID NO 4
<211> LENGTH: 1050
<212> TYPE: RNA
<213> ORGANISM: homo sapiens
<220> FEATURE:
<223> OTHER INFORMATION: synthetically generated cRNA

<400> SEQUENCE: 4 gggaugggu gagauuuccu uuuagguacu aaggucgacc aagagguugu cagacagggu      60
uuggcugggc cagcaagacu ugacaacucc cucuaccuaa ccagcugccc aacuguagaa    120
acuaccaacc caccagccaa caggagagg gagagggaac aggcacccuc aagggguca      180 aguuuuagac cccauguaau aaaggugu uucaaggcca gaugacauu auuucauuaa       240 cccucacaau gcacucugug agguaggugc aaaugccagc auucacaga uaugggccuu     300 gaaguuagag aaaauucaac augagggaca gcuucccugg uuaguacggu gaaguggggcc   360 ccuaccuacc uagaaugugg cugauuguaa acuaaccccuu aacugcaaga acauuucuua   420
caucucccaa acaucccuca caguaaaaac cuuaaaaucu aagcugguau guccuacucc    480
ccauccuccu ccccacaaca aaacaccagu gcaggccaac uuguucagug gagcccggg     540 acaaagcaaa uggaaguccu gggugcuucu gacgcacacc uauugcaagc aagggguucaa   600 agacccaaaa cccaaaaugg caggggaggg agagaugggg gagggaggcu gucaguggg     660 aacaagaagu ggagaauguc agucugaguc aggcccuucu gucuugaaca ugaguuuuuu    720
auggcgggag guagacugac ccuuuuugga cuucaggugg cuggagugag cccugcuccc    780
cccuggcucc uucccagccu gggcauccuu gaguccaag gccucauuca gcucucggaa     840
caucucgaag cgcucacgcc cacggaucug aaggugaaa uauuucccau ccaguggguuu    900 cuucuuuggc uggggagagg agcuggugu guugggcagu gcucgcuuag ugcucccugg    960
gggcagcucg uggugaggcu ccccuuucuu gcggagauuc ucuuccucug ugcgccgguc   1020
ucucccagga caggcacaaa cacgcaccuc                                    1050

<210> SEQ ID NO 5
<211> LENGTH: 25
<212> TYPE: DNA
<213> ORGANISM: Artificial Sequence
<220> FEATURE:
<223> OTHER INFORMATION: synthetic probe

<400> SEQUENCE: 5
cagaggaaga gaatctccgc aagaa                                           25

<210> SEQ ID NO 6
<211> LENGTH: 25
<212> TYPE: DNA
<213> ORGANISM: Artificial Sequence
<220> FEATURE:
<223> OTHER INFORMATION: synthetic probe

<400> SEQUENCE: 6
gaatctccgc aagaaagggg agcct                                           25

<210> SEQ ID NO 7
<211> LENGTH: 25
<212> TYPE: DNA
```

```
<213> ORGANISM: Artificial Sequence
<220> FEATURE:
<223> OTHER INFORMATION: synthetic probe

<400> SEQUENCE: 7
cgagctgccc ccagggagca ctaag                                    25

<210> SEQ ID NO 8
<211> LENGTH: 25
<212> TYPE: DNA
<213> ORGANISM: Artificial Sequence
<220> FEATURE:
<223> OTHER INFORMATION: synthetic probe

<400> SEQUENCE: 8
ccagggagca ctaagcgagc actgc                                    25

<210> SEQ ID NO 9
<211> LENGTH: 25
<212> TYPE: DNA
<213> ORGANISM: Artificial Sequence
<220> FEATURE:
<223> OTHER INFORMATION: synthetic probe

<400> SEQUENCE: 9
tgaatgaggc cttggaactc aagga                                    25

<210> SEQ ID NO 10
<211> LENGTH: 25
<212> TYPE: DNA
<213> ORGANISM: Artificial Sequence
<220> FEATURE:
<223> OTHER INFORMATION: synthetic probe

<400> SEQUENCE: 10
aaggatgccc aggctgggaa ggagc                                    25

<210> SEQ ID NO 11
<211> LENGTH: 25
<212> TYPE: DNA
<213> ORGANISM: Artificial Sequence
<220> FEATURE:
<223> OTHER INFORMATION: synthetic probe

<400> SEQUENCE: 11
aggctgggaa ggagccaggg gggag                                    25

<210> SEQ ID NO 12
<211> LENGTH: 25
<212> TYPE: DNA
<213> ORGANISM: Artificial Sequence
<220> FEATURE:
<223> OTHER INFORMATION: synthetic probe

<400> SEQUENCE: 12
ggagccaggg gggagcaggg ctcac                                    25

<210> SEQ ID NO 13
<211> LENGTH: 25
<212> TYPE: DNA
<213> ORGANISM: Artificial Sequence
<220> FEATURE:
<223> OTHER INFORMATION: synthetic probe

<400> SEQUENCE: 13
tgggctacac tgagcaccag gtggt                                    25
```

<210> SEQ ID NO 14
<211> LENGTH: 25
<212> TYPE: DNA
<213> ORGANISM: Artificial Sequence
<220> FEATURE:
<223> OTHER INFORMATION: synthetic probe

<400> SEQUENCE: 14
aatatgatga catcaagaag gtggt                                      25

<210> SEQ ID NO 15
<211> LENGTH: 25
<212> TYPE: DNA
<213> ORGANISM: Artificial Sequence
<220> FEATURE:
<223> OTHER INFORMATION: synthetic probe

<400> SEQUENCE: 15
atccctgagc tagacgggaa gctca                                      25

<210> SEQ ID NO 16
<211> LENGTH: 25
<212> TYPE: DNA
<213> ORGANISM: Artificial Sequence
<220> FEATURE:
<223> OTHER INFORMATION: synthetic probe

<400> SEQUENCE: 16
aactgtggcg tgatggccgc ggggc                                      25

<210> SEQ ID NO 17
<211> LENGTH: 25
<212> TYPE: DNA
<213> ORGANISM: Artificial Sequence
<220> FEATURE:
<223> OTHER INFORMATION: synthetic probe

<400> SEQUENCE: 17
gtgtgaacca tgagaagtat gacaa                                      25

<210> SEQ ID NO 18
<211> LENGTH: 25
<212> TYPE: DNA
<213> ORGANISM: Artificial Sequence
<220> FEATURE:
<223> OTHER INFORMATION: synthetic probe

<400> SEQUENCE: 18
ttcgtcatgg gtgtgaacca tgaga                                      25

<210> SEQ ID NO 19
<211> LENGTH: 1034
<212> TYPE: RNA
<213> ORGANISM: Arabidopsis thaliana

<400> SEQUENCE: 19
ggguaccaga gcucccuagg uucuagagcg gccgcccuuu uuuuuuuuu uuagaauuca      60 agcucacacg agcauucgau caccaagaca auuacagga auucacaaau cugucuuuca    120
uuacacagug uuuuugauac acauaaagcu cauaagguac acauauuucu auuuuuacau    180
ucauuaguug aaagggauaa caauaucgcc aauguuguug ugccauggau ccgccaagug    240
aguugccaag uucccaaug guccugucc cggguaagcc gacuguugca cacagaauuc    300

```
uacaaacgcc aacagcgcaa gccgcccguu cuugaucucu uuaacuuuca auuccucgag      360
cuucuugggg uccuucgagu auccaagagg gucaaaugcg ccucccgggu acuucuucuu      420 cucaggucu uucuccauac uucucuggug cucaacaaau gcaauggcua agaacucaau       480
ggccaagauu guggcaaag uaccccacgg gacugguuu cccaaguaag uggcuugacc        540
cccugguagu gcugcccauu ccugagccuu aacccaguuu ccauaccua augcuucugg      600 uaccaaaauc ccaggaacag cgagcauagc ccaucuacag uggaugagcu cugacucuuu    660
guaucucuca agguucgcug gaacuucccc aaguccaagu gggucaaacc caaagucacc     720
aggagcagaa ccgucaaggu aagcggucg uggcucgcca gcauccagu gagcagccau       780 ucugauacga ccaacauucc cggcguuugg gaguggaacu ccggcggaua cgaauuuaga     840
cuuggaagaa gagagaagcg aagggguacac ggcggcuaug ccacagcuca uaagcgaguu   900
cgacgccauc guuucucucu aucugucgga cgcgugggguc gacccgggaa uuccggaccg    960
guaccugcag gaauuccucg agaccguacg ugcgcgcgaa ugcauccaga ucuucccucu    1020
agucaaggcc uuaa                                                      1034

<210> SEQ ID NO 20
<211> LENGTH: 1012
<212> TYPE: RNA
<213> ORGANISM: Arabidopsis thaliana

<400> SEQUENCE: 20
gggcagaucu ucgaaugcau cgcgcgcacc guacgucucg aggaauuccu gcaggauauc      60
uggauccacu aguaacggcc gccagugugc uggaauucgc ccuuucacaa aacacagcga    120 augcccacu cccacaucau uauucauucu uuaaccauuu ugcuuaauca ucagacucuu     180 uuucuucuu cacuuccucu ucaguggucu uggcaugaua accuggaagc uucucuuuga    240
ucuuuuccaa aauccccuuc uucuccuccg gauguuccac uggaagcccc gucguaggcu    300
ccaccggaug ucccguuaca accaacggcg uggacgugac agcuggugaa ccucugcuu    360 ucucgucgug gugaccagga agcuucccuu ugaucuucuc aacuaauccu ucuucucuu    420 ccucgggaug gucaugcucc accacacucu ccgacacugg uaccgggaug guaguggaaa    480
cugguacauc auccccuguc gucuguccg gguguccuggg gagcuucccc uugaucuucu   540 ccacuaguc uuucuuaucu ucccucccuu caacgaucuu cuucuucuuc ccuucuuuu    600 ccucaccuuc uucaucgcuc gaagaggaag aagagcuguu ggaucggug agcuuuucga     660 ugacacuagg cuuguucucc ucaucuuccu cggucuuuuc uugaagcucc uuagcagag    720 uaaucuuguu cuccuucacu uccucgugcu ccgcagcuaa cuccgguuca gagaucugag   780
ccuuaugauc gaacucagac ucgagcgucg uugucucuug agguuucacu uccucuuccu   840
ucuuccccaa gaaaucaaac aauccacgau ccguaaccuc uguugucguc gcggugauu    900 ccucuguugc gaccgaaggg cgaauucgc agauauccau cacacuggcg gccgcucgag   960
caugcaucua gauaccuagg ugagcucugg uaccucucua gucaaggccuu aa         1012

<210> SEQ ID NO 21
<211> LENGTH: 1204
<212> TYPE: RNA
<213> ORGANISM: Arabidopsis thaliana

<400> SEQUENCE: 21
ggguaccaga gcucccuagg uucuagaacc ggugacgucu cccaugguga agcuuggauc      60
cacuaguaac ggccgccagu gugcuggaau ucgcccuuga ucucuuuuc ccguucuccg     120
```

-continued

| | |
|---|---:|
| aguguugcac uuauaagcuu gcuuacuucc uccuugagug ccaaaucauc auacccgugc | 180 |
| cacggauugu ucuccaaacg aguauccgca auguaacugu gaugaguuuc uccagggaga | 240 |
| ccauucaaag aaggaaaugc aucucugucu agagaaaaua cuuugcuuac agccucuguu | 300 |
| gcauuucuaa cuuucuucug cgacauguuu agagacucug caauccuauc aauggagggu | 360 |
| gugauuccuu ucucuugaag ucuaagcuuu gcauuucgga uuaaaccgag ucuucaugu | 420 |
| aggugaguag guaaccucaa gguucuugag uuguccacua gugcucuuga gacacccugu | 480 |
| cgaauccacc aauauacaua aguugaaauu cugaaaccuu uggaagaauc aaauuucucu | 540 |
| auuccccgca aaguccgau aagaccaccc ugaacaaggu cagacauuuc ugcucccaaa | 600 |
| uuaucauaac gcugagcaau agacauaacc aaacgcacau acucauagc caacuucucu | 660 |
| cuagcuagau gacacuccau caaccacgcc ugaagcucgg cccgagauau cuucaaagau | 720 |
| acugcaagcu guucaucaga aggcucacag ccuaaucuau ccuucaaucu ugacuuauga | 780 |
| ucaucaagac gaagaccaga uuugauuuuc uuagacaagc gcacaacuuc cacaugacua | 840 |
| agcacaucuu cacuuauuac accuuucaca uaaccucuaa cuugcuuucc acuagaaaca | 900 |
| ucagaaacug cuuuaacaug agucauauua guuuucuucu uagcaccaau ccuucuuuga | 960 |
| cgagcugaaa ucccugaaca ggugauaacc ggaaucuucu ucuuccguau agucccccuug | 1020 |
| cccggauacu cacucgacac cgccuuuuca aaugaaagau uccaacuuuu ucuaacaua | 1080 |
| gacuucugua acaguaaaau ugccucaaag ggcgaauucu gcagauaucc aucacacugg | 1140 |
| cggccgcucg agaccguacg ugcgcgcgaa ugcauccaga ucuucccucu agucaaggcc | 1200 |
| uuaa | 1204 |

<210> SEQ ID NO 22
<211> LENGTH: 1394
<212> TYPE: RNA
<213> ORGANISM: Escherichia coli

<400> SEQUENCE: 22

| | |
|---|---:|
| gggcagaucu ucgaaugcau cgcgcgcacc guacgucucg aggaauuccu gcaggauauc | 60 |
| uggauccacu aguaacggcc gccagugugc uggaauucgc ccuuagcgcc gccgagaaug | 120 |
| agugaaagau ucggcgcagc accguuggc aaauauaacg gcaauccaac auugcguaac | 180 |
| uuugccgcaa accguuucgg uccauaggcu uccagcaccu gcacagcagg uaaguucagc | 240 |
| gagcgcacca gcgccucgcu caugcugauc gggccaugaa aaccgcuauc aaaguuaccu | 300 |
| ggucgauaau caccggugcg ccgggggacg ucuugcagca gugaugccgg guggaucaag | 360 |
| ccuucaucca gcgccagacc auaaacaaac gguuugagca cugauccugg cgaucggauc | 420 |
| gaauugacca uaucaacaug accaaagcgu gaaucaucgu ugagaucaac cgaucccacc | 480 |
| cagccgcgaa cacgcauauc gguaugauca ccacgauca ucgccaguga gcugcgcggu | 540 |
| ggcaaccgcc cuuccaguu uugcgccagu ucuuccagac gucguugaag accggcaucc | 600 |
| aacuaguag ugauuuuguc gcuuuugcuu uuaccgagca ucaugcgcga aaacagcggu | 660 |
| gccaguugcg gcauuugucg ggggccagc cagaugggu cuucccuuga cucuuuuacc | 720 |
| ugcucacggg accacacacc uugcacggcc auccguucga gcacuuuauu acgcgcggcu | 780 |
| ucggcacgcu ccgccaacg auccgggcga agacggcugg gcgcuugcgg caaaaccgcc | 840 |
| agcauugccg ccucggaaua gcuuaaauuc gcaggcgauu uucgagauaa gcccaacuuu | 900 |
| gccgcaccga uccccugcaa cguaccgcca aacggagcgc gguuaagaua caaggucaga | 960 |

| | |
|---|---:|
| auuucacgcu uagacagaug ccauuccagu ugcaacgcgc gccagagcug gcgaauuuug | 1020 |
| ccgccaaaug uuuggggug aggaucaagc agacgagcaa ccugcauagu gagcgugcug | 1080 |
| ccaccggaaa uaacccgucc cgaagugaga ucuugccaug cugcgcgcgc caccgagaau | 1140 |
| ggauucaccc ccggaugcuu ccagaaccag cgaucuucau aauugaucag cgcuucaagg | 1200 |
| uaacguggag aaacaucuuc gauuguuacc ggauaacgcc agaugccguc agcaucggcg | 1260 |
| aagcgccaga gcggcguacc auccugcgcc acgaccaaag gcgaauucu gcagauaucc | 1320 |
| aucacacugg cggccgcucg agcaugcauc uagauaccua ggugagcucu gguacccucu | 1380 |
| agucaaggcc uuaa | 1394 |

<210> SEQ ID NO 23
<211> LENGTH: 1392
<212> TYPE: RNA
<213> ORGANISM: Escherichia coli

<400> SEQUENCE: 23

| | |
|---|---:|
| gggcagaucu ucgaaugcau cgcgcgcacc guacgucucg aggaauuccu gcaggauauc | 60 |
| uggauccacu aguaacggcc gccagugugc uggaauucgc ccuucaguu aacguucgc | 120 |
| cauucagaaa ccaccagcgu ucaccugccc cuccacuuga uugcaacggc aaagucgcuu | 180 |
| ccgcugcgcc cgguaaacgu uaauaaucg cgccaucgcg aacgccguc agcugcagcg | 240 |
| ggagcugggc aucgugaccg uauggcgggc aacuugucga ggccgguggu aagcgcacag | 300 |
| cgcgacguuc ugaugcgggc agccaggguu ccagcgguag cggccagaca uuuaucauuu | 360 |
| cuugucgcgc uugcgggcaa ucagcggcaa cacguuugcc auuucaucc agccagaugg | 420 |
| ggaaacgaau gccauuaaug ccuuccugcu ccggcaguaa uagaguuggc ggcugacucc | 480 |
| cguccagcag ccagguugcc aggcggcggc gacaguuacc gucaccuucc ggcaaagacu | 540 |
| guccgcccgg ccagcagaua acgccacgag ugacugaguu cgggcgcggg ucuuccggca | 600 |
| gauucgcacu gcgcgacagu aagauauuau ugaccugauu caacaauggu acggcacugg | 660 |
| caaagccaaa cugaccaaca acgggcgugc cguccggucu gccaguccag aucccaauga | 720 |
| cauagcgagc guuaacccca aucgcccagg cgucacgaua gccauagcug gugcccguuu | 780 |
| uccaugccag uggggcgacg cgcggcaagg cacuauccgg caagguugc gcuucaucag | 840 |
| ccauaauccg gcgaaugauc cacgccgccc ccgacgacau uaaaggccgu ucaagcagcg | 900 |
| gaucgucagg cuguaagcgc aauuugccug ccuugccgug gcgagcaaac gcgguauacg | 960 |
| cugccgccau aucuuccagu uuugcaccag cgccgccgag aaugagugaa agauucggcg | 1020 |
| cagcaccguu gggcaaauau aacggcaauc caacauugcg uaacuuugcc gcaaaccguu | 1080 |
| ucgguccaua ggcuuccagc accugcacag cagguaaguu cagcgagcgc accagcgccu | 1140 |
| cgcucaugcu gaucgggcca ugaaaaccgc uaucaaaguu accggucga uaucaccgg | 1200 |
| ugcgccgggg gacgucuugc agcagugaug ccggguggau caagccuuca uccagcgcca | 1260 |
| gaccauaaac aaacgguuug agcacugauc cuggcaaggg cgaauucugc agauauccau | 1320 |
| cacacuggcg gccgcucgag caugcaucua gauaccuagg ugagcucugg uacccucuag | 1380 |
| ucaaggccuu aa | 1392 |

<210> SEQ ID NO 24
<211> LENGTH: 16
<212> TYPE: DNA
<213> ORGANISM: Artificial Sequence
<220> FEATURE:
<223> OTHER INFORMATION: synthetic probe

```
<400> SEQUENCE: 24
gctagcgaaa gctagc                                                    16

<210> SEQ ID NO 25
<211> LENGTH: 16
<212> TYPE: DNA
<213> ORGANISM: Artificial Sequence
<220> FEATURE:
<223> OTHER INFORMATION: synthetic probe

<400> SEQUENCE: 25
gcgagcgaaa gcgagc                                                    16

<210> SEQ ID NO 26
<211> LENGTH: 16
<212> TYPE: DNA
<213> ORGANISM: Artificial Sequence
<220> FEATURE:
<223> OTHER INFORMATION: synthetic probe

<400> SEQUENCE: 26
gcaggcgaaa gcaggc                                                    16

<210> SEQ ID NO 27
<211> LENGTH: 16
<212> TYPE: DNA
<213> ORGANISM: Artificial Sequence
<220> FEATURE:
<223> OTHER INFORMATION: synthetic probe

<400> SEQUENCE: 27
gcaggggaaa gcaggc                                                    16

<210> SEQ ID NO 28
<211> LENGTH: 16
<212> TYPE: DNA
<213> ORGANISM: Artificial Sequence
<220> FEATURE:
<223> OTHER INFORMATION: synthetic probe

<400> SEQUENCE: 28
gcataccgaa gcacgc                                                    16

<210> SEQ ID NO 29
<211> LENGTH: 20
<212> TYPE: DNA
<213> ORGANISM: Artificial Sequence
<220> FEATURE:
<223> OTHER INFORMATION: synthetic probe

<400> SEQUENCE: 29
aaccatgaga agtatgacaa                                                20

<210> SEQ ID NO 30
<211> LENGTH: 15
<212> TYPE: DNA
<213> ORGANISM: Artificial Sequence
<220> FEATURE:
<223> OTHER INFORMATION: synthetic probe

<400> SEQUENCE: 30
tgagaagtat gacaa                                                     15

<210> SEQ ID NO 31
```

```
<211> LENGTH: 10
<212> TYPE: DNA
<213> ORGANISM: Artificial Sequence
<220> FEATURE:
<223> OTHER INFORMATION: synthetic probe

<400> SEQUENCE: 31
agtatgacaa                                                             10

<210> SEQ ID NO 32
<211> LENGTH: 5
<212> TYPE: DNA
<213> ORGANISM: Artificial Sequence
<220> FEATURE:
<223> OTHER INFORMATION: synthetic probe

<400> SEQUENCE: 32 gacaa                                                                   5

<210> SEQ ID NO 33
<211> LENGTH: 25
<212> TYPE: DNA
<213> ORGANISM: Artificial Sequence
<220> FEATURE:
<223> OTHER INFORMATION: synthetic probe

<400> SEQUENCE: 33
aggagaacaa gattactctg ctaga                                            25

<210> SEQ ID NO 34
<211> LENGTH: 25
<212> TYPE: DNA
<213> ORGANISM: Artificial Sequence
<220> FEATURE:
<223> OTHER INFORMATION: synthetic probe

<400> SEQUENCE: 34
ttcgtttccc catctggctg gatga                                            25

<210> SEQ ID NO 35
<211> LENGTH: 25
<212> TYPE: DNA
<213> ORGANISM: Artificial Sequence
<220> FEATURE:
<223> OTHER INFORMATION: synthetic probe

<400> SEQUENCE: 35
ggttatttcc ggtggcagca cgctc                                            25

<210> SEQ ID NO 36
<211> LENGTH: 16
<212> TYPE: DNA
<213> ORGANISM: Artificial Sequence
<220> FEATURE:
<223> OTHER INFORMATION: synthetic probe

<400> SEQUENCE: 36
gctagcgaaa gctagc                                                      16

<210> SEQ ID NO 37
<211> LENGTH: 60
<212> TYPE: DNA
<213> ORGANISM: Artificial Sequence
<220> FEATURE:
<223> OTHER INFORMATION: synthetic probe

<400> SEQUENCE: 37
```

```
gctagcgcgc gcgcgcgcgc gcgcgcgcga aagcgcgcgc gcgcgcgcgc gcgcgctagc    60

<210> SEQ ID NO 38
<211> LENGTH: 22
<212> TYPE: DNA
<213> ORGANISM: Artificial Sequence
<220> FEATURE:
<223> OTHER INFORMATION: synthetic probe

<400> SEQUENCE: 38
gctagctagc tagctagcta gc                                              22

<210> SEQ ID NO 39
<211> LENGTH: 60
<212> TYPE: DNA
<213> ORGANISM: Artificial Sequence
<220> FEATURE:
<223> OTHER INFORMATION: synthetic probe

<400> SEQUENCE: 39
gctagctagc tagctagcta gctagcgcga aagctagcta gctagctagc tagctagcgc    60

<210> SEQ ID NO 40
<211> LENGTH: 16
<212> TYPE: DNA
<213> ORGANISM: Artificial Sequence
<220> FEATURE:
<223> OTHER INFORMATION: synthetic probe

<400> SEQUENCE: 40
gctagcgaaa gctagc                                                     16

<210> SEQ ID NO 41
<211> LENGTH: 6
<212> TYPE: DNA
<213> ORGANISM: Artificial Sequence
<220> FEATURE:
<223> OTHER INFORMATION: synthetic probe

<400> SEQUENCE: 41 gctagc                                                                6

<210> SEQ ID NO 42
<211> LENGTH: 60
<212> TYPE: DNA
<213> ORGANISM: Artificial Sequence
<220> FEATURE:
<223> OTHER INFORMATION: synthetic probe

<400> SEQUENCE: 42
gctagctagc tagctagcta gcgctagcga aagctagcgc tagctagcta gctagctagc    60

<210> SEQ ID NO 43
<211> LENGTH: 8
<212> TYPE: DNA
<213> ORGANISM: Artificial Sequence
<220> FEATURE:
<223> OTHER INFORMATION: synthetic probe

<400> SEQUENCE: 43 tttttttt                                                              8

<210> SEQ ID NO 44
<211> LENGTH: 18
<212> TYPE: DNA
```

```
<213> ORGANISM: Artificial Sequence
<220> FEATURE:
<223> OTHER INFORMATION: synthetic probe

<400> SEQUENCE: 44
gctagctagc tagctagc                                                    18

<210> SEQ ID NO 45
<211> LENGTH: 60
<212> TYPE: DNA
<213> ORGANISM: Artificial Sequence
<220> FEATURE:
<223> OTHER INFORMATION: synthetic probe

<400> SEQUENCE: 45
gctagctagc tagctagcgc tagcgaaagc tagcgctagc tagctagcta gcttttttt     60

<210> SEQ ID NO 46
<211> LENGTH: 44
<212> TYPE: DNA
<213> ORGANISM: Artificial Sequence
<220> FEATURE:
<223> OTHER INFORMATION: synthetic probe

<400> SEQUENCE: 46
gctagctagc tagcgctagc gaaagctagc gctagctagc tagc                       44

<210> SEQ ID NO 47
<211> LENGTH: 44
<212> TYPE: DNA
<213> ORGANISM: Artificial Sequence
<220> FEATURE:
<223> OTHER INFORMATION: synthetic probe

<400> SEQUENCE: 47
gctagctagc gctagcgaaa gctagcgcta gctagctttt tttt                       44

<210> SEQ ID NO 48
<211> LENGTH: 36
<212> TYPE: DNA
<213> ORGANISM: Artificial Sequence
<220> FEATURE:
<223> OTHER INFORMATION: synthetic probe

<400> SEQUENCE: 48
gctagctagc gctagcgaaa gctagcgcta gctagc                                36

<210> SEQ ID NO 49
<211> LENGTH: 36
<212> TYPE: DNA
<213> ORGANISM: Artificial Sequence
<220> FEATURE:
<223> OTHER INFORMATION: synthetic probe

<400> SEQUENCE: 49
gctagcgcta gcgaaagcta gcgctagctt tttttt                                36

<210> SEQ ID NO 50
<211> LENGTH: 25
<212> TYPE: DNA
<213> ORGANISM: Artificial Sequence
<220> FEATURE:
<223> OTHER INFORMATION: synthetic probe

<400> SEQUENCE: 50
ctagcgctag cgaaagctag cgcta                                            25
```

```
<210> SEQ ID NO 51
<211> LENGTH: 25
<212> TYPE: DNA
<213> ORGANISM: Artificial Sequence
<220> FEATURE:
<223> OTHER INFORMATION: synthetic probe

<400> SEQUENCE: 51
gctagcgaaa gctagctttt ttttt                                              25

<210> SEQ ID NO 52
<211> LENGTH: 24
<212> TYPE: DNA
<213> ORGANISM: Artificial Sequence
<220> FEATURE:
<223> OTHER INFORMATION: synthetic probe

<400> SEQUENCE: 52
gcgcgctagc gaaagctagc gcgc                                               24

<210> SEQ ID NO 53
<211> LENGTH: 60
<212> TYPE: DNA
<213> ORGANISM: Artificial Sequence
<220> FEATURE:
<223> OTHER INFORMATION: synthetic probe

<400> SEQUENCE: 53
gctagcgaaa gctagctttt cgatcggaaa cgatcgtttt ccagtgacga aagtcactgg        60
```

ARRAYS HAVING BACKGROUND FEATURES AND METHODS FOR USING THE SAME

CROSS REFERENCE TO RELATED APPLICATIONS

This application is a continuation in part of application Ser. No. 09/398,399 filed on Sep. 17, 1999; the disclosure of which is herein incorporated by reference.

TECHNICAL FIELD

The technical field of this invention is mircoarrays, particularly nucleic acid microarrays.

BACKGROUND OF THE INVENTION

In nucleic acid sequencing and analysis, there is a growing emphasis on the use of high density arrays of immobilized nucleic acid probes. Such arrays can be prepared by massively parallel schemes, e.g., using the selective photomask techniques described in U.S. Pat. No. 5,143,854. Arrays constructed in this manner are typically formed in a planar area of between about 4–100 mm$^2$, and can have densities of up to several hundred thousand or more distinct array members per cm$^2$.

In use, an array surface is contacted with one or more analytes under conditions that promote specific, high-affinity binding of the analyte molecules to one or more of the array members (probes). The goal of the procedure is to identify one or more position-addressable members of the array which bind to the analyte as a method of detecting analyte molecule(s). Typically, the analyte is labeled with a detectable label such as a fluorescent tag, to indicate the one or more array regions where analyte binding to the array occurs. A variety of biological and/or chemical compounds have been used as hybridization probes in the above-described arrays. See, generally, Wetmur, J. (1991) *Crit Rev Biochem and Mol Bio* 26:227.

For example, such arrays can be used to perform nucleic acid hybridization assays. Generally, in such a hybridization assay, labeled single-stranded analyte nucleic acid (e.g. polynucleotide target) is hybridized to a complementary single-stranded nucleic acid probe. The complementary nucleic acid probe binds the labeled target and the presence of the target polynucleotide of interest is detected.

A common drawback of nucleic acid hybridization assays is the presence of signals which are generated due to an undesirable interaction of various components used in a given assay, i.e. signal generated by entities other than due to hybridization of the analyte and the specified complementary probes, such as signal generated from (i) the reporter, i.e. a signal arising from the label itself when it is not attached to the target, such as a signal generated from a fluorescent dye used in labeling the target; (ii) the non-reporter, i.e. a signal generated from the substrate or other assay components, and (iii) signal generated due to non-specific binding of probes to labeled entities other than their specific target molecules, i.e. binding not related to hybridization of the analyte and the complementary probes. Background signal generated from any of these mechanisms will add to the total signal measured. Uncorrected signal containing background signal results in an overestimation of the "real" signal, which can lead to "false positive" results. Thus, the background signal needs to be estimated accurately and subtracted from the total signal of a hybridization assay to yield the "real" signal.

However, accurate estimation of the background signal is complicated. Underestimation of the background signal will result in an overestimation of the "real" signal, which can yield "false positive" results. Conversely, overestimation of the background signal will result in an underestimation of the "real" signal, which can yield "false negative" results. Thus, background overestimation will negatively impact the lowest concentration of the target that can be reliably detected. An accurate estimate of the background signal is thus needed to generate accurate results.

A common approach to correcting background signal in arrays is to evaluate the portion of the array that is outside of the probe features. However, the background correction problem is particularly complex for measurements made using arrays of nucleic acid hybridization probes, because background may vary as a function of location on the surface. Furthermore, the local properties of the surface that contains bound nucleic acid probes may be very different from the surrounding surface that does not contain bound probes. The "local background signal" is the signal generated from the portion of the array outside of the probe feature area. The signal from the local background immediately adjacent to a given feature is subtracted from the total signal of that feature to correct for background and to yield the "real" signal. Alternatively, the local background signal from the entire array can be evaluated and a single value (e.g. an average local background signal or the minimum local background signal) can be calculated to correct all features of that array. This is referred to as the "global background signal." The choice of an appropriate background correction method depends critically upon which of these two influences, i.e., local background or modification of surface properties by covalently bound nucleic acid probes, is judged to most strongly influence background signal in the array regions containing covalently bound probe molecules.

The use of local or global background correction methods are problematic. The properties of the array surface outside the features may differ from the properties of the array surface within the features. These differences can result in different levels of non-reporter signal or different levels of reporter non-specific binding. Thus, the observed signal from the local background or estimated from a global background calculation may result in an inaccurate estimation of the background signal within the feature. Additionally, the probes themselves may generate a portion of the background signal. For example, the bases or phosphodiester linkages of the probes may (i) produce non-reporter signal, (ii) bind to components that produce non-reporter signal, or (iii) non-specifically bind the reporter. Therefore, in these cases, using local background will underestimate the true background signal that should be subtracted.

Representative methods for resolving the problem of interfering background signals in nucleic acid hybridization assays are described in U.S. Pat. Nos. 4,868,105; 5,124,246; 5,563,034; and 5,681,702; WO 98/24933; Chen Y., et al., *Journal of Biomedical Optics* (1997) 2:364–374; and DeRisi J. L. et al. (1997) *Science* 278:680–686. Existing methods generally correct for background signal by subtracting either the local or global background. However, these methods do not involve surface-bound nucleic acid probes, and in some cases background estimates obtained from local or global sampling of nonprobe regions overestimate background in regions that contain probes. Background overestimation negatively impacts the lowest dose of the target that can be reliably detected by an array involving a nucleic acid hybridization assay, i.e., the lower limit of detection or LLD of the assay.

Therefore, there is a continued need for the development of reliable methods for estimating background signal from probe-containing regions in hybridization arrays during hybridization assays.

SUMMARY OF THE INVENTION

Nucleic acid arrays that have background features, as well as methods for using the same, are provided. The subject nucleic acid arrays include both hybridization features and background features, where the background features provide a background signal in a hybridization assay that is made up of a feature substrate component, a nucleic acid probe component and a nucleic acid probe non-specific binding component. In practicing the subject methods, the arrays are contacted with a sample and signals are observed for both hybridization features and background features. The background feature signal is then subtracted from the hybridization feature signal to obtain a background corrected hybridization feature signal that is employed as the output of the assay, e.g., to determine the presence, either quantitatively or qualitatively, of the analyte target nucleic acid in the sample. Also provided are kits for use in practicing the subject methods.

In one embodiment, the invention provides a set of features comprising polymeric probes, e.g., oligophosphodiester probes, wherein the features comprise hybridization features comprising hybridization probes that selectively hybridize to a detectably labeled target nucleotide sequence, and background features comprising background probes that do not selectively hybridize to the target nucleotide sequence, and further wherein the probes may be in solution or are bound to a surface. The target analyte nucleotide sequence may be labeled with a detectable label prior to, or after hybridization, preferably prior to hybridization. In one embodiment, the target nucleotide sequence is directly labeled with a detectable label. In an alternative embodiment, the target nucleotide sequence is indirectly labeled with a detectable label prior to, or after hybridization, preferably prior to hybridization. In a preferred embodiment, the set of probes is bound to an array surface. In another preferred embodiment, the background probe is selected from the group consisting of empirically observed inactive probes, probes forming stable intramolecular structures, short probes, probes comprising reverse polarity nucleotide analogs and probes comprising abasic phosphodiesters or modified nucleotidic units.

In an additional embodiment, the invention provides a method of detecting the presence and/or amount of a target nucleotide sequence (i.e., analyte) in an fluid sample. The method of the invention comprises the following:

(a) providing a sample suspected of containing the target nucleotide sequence;

(b) contacting an aliquot of the fluid sample suspected of containing the target nucleotide sequence with a set of features comprising polymeric probes, e.g., oligophosphodiester probes, wherein the target nucleotide sequence is labeled with a detectable label capable of generating a measurable signal, and further wherein the features comprise:

(i) hybridization features comprising hybridization probes that selectively hybridize to the target nucleotide sequence, and (ii) background features comprising background probes that do not selectively hybridize to the target nucleotide sequence;

(c) detecting an observed signal, wherein the observed signal is an amount of signal generated from contacting the target nucleotide sequence with said features comprising polymeric, e.g., oligophosphodiester, probes;

(d) detecting a background signal, wherein the background signal is an amount of signal generated from the background features; and (e) subtracting the background signal from the observed signal to determine the presence and/or amount of the target nucleotide sequence in the analyte.

In a preferred embodiment, the method involves the use of a set of probes bound to an array surface. In an additional preferred embodiment, the method involves the use of background probes that mimic nonspecific binding, while not preventing the binding of target to the hybridization probes. In more preferred embodiments, the background probe is selected from the group consisting of empirically observed inactive probes, probes forming stable intramolecular structures, short probes, probes comprising reverse polarity nucleotide analogs and probes comprising abasic phosphodiesters or modified nucleotidic units.

In certain embodiments, the label is detected using calorimetric, fluorimetric, chemiluminescent or bioluminescent means. Thus, the label can be, for example, a fluorescent compound, i.e., capable of emitting radiation (visible or invisible) upon stimulation by radiation of a wavelength different from that of the emitted radiation, or through other manners of excitation, e.g. chemical or non-radiative energy transfer. The label may be a fluorescent dye associated with a nucleic acid.

In another embodiment, the present invention is directed to a method for estimating background noise encountered in a nucleic acid hybridization assay.

In another embodiment, the present invention is directed to a method of validating a test-background feature comprising test-background probes. The method of the invention comprises the following:

(a) providing a sample containing the target nucleotide sequence;

(b) contacting an aliquot of the sample containing the target nucleotide sequence with a set of features comprising polymeric probes, e.g., oligophosphodiester probes, wherein the target nucleotide sequence is labeled with a detectable label capable of generating a measurable signal, and further wherein the features comprise (i) hybridization features comprising hybridization probes that selectively hybridize to the target nucleotide sequence, (ii) test-background features comprising test-background probes that do not selectively hybridize to the target nucleotide sequence, and (iii) standard-background features comprising standard-background probes that do not selectively hybridize to the target nucleotide sequence;

(c) detecting an observed signal, wherein the observed signal is an amount of signal generated from contacting the target nucleotide sequence with said features comprising oligophosphodiester probes;

(d) detecting a test-background signal, wherein the test-background signal is an amount of signal generated from the test-background features;

(e) detecting a standard-background signal, wherein the standard-background signal is an amount of signal generated from the standard-background features; and (f) comparing the amount of the test-background signal with the amount of the standard-background signal.

Finally, the invention encompasses test kits for detecting the presence and/or amount of a target nucleotide sequence in an analyte. The kit comprises a container containing an array of features comprising polymeric, e.g., oligophosphodiester probes, wherein the features comprise hybridization features comprising hybridization probes that selectively hybridize to a target nucleotide sequence, and background features comprising background probes that do not selectively hybridize to the target nucleotide sequence.

These and other embodiments of the present invention will readily occur to those of ordinary skill in the art in view of the disclosure herein.

BRIEF DESCRIPTION OF THE DRAWINGS

FIG. 5 depicts various abasic phosphoramidite structures which can be used to produce background probes of the present invention.

DEFINITIONS

Figure 1:
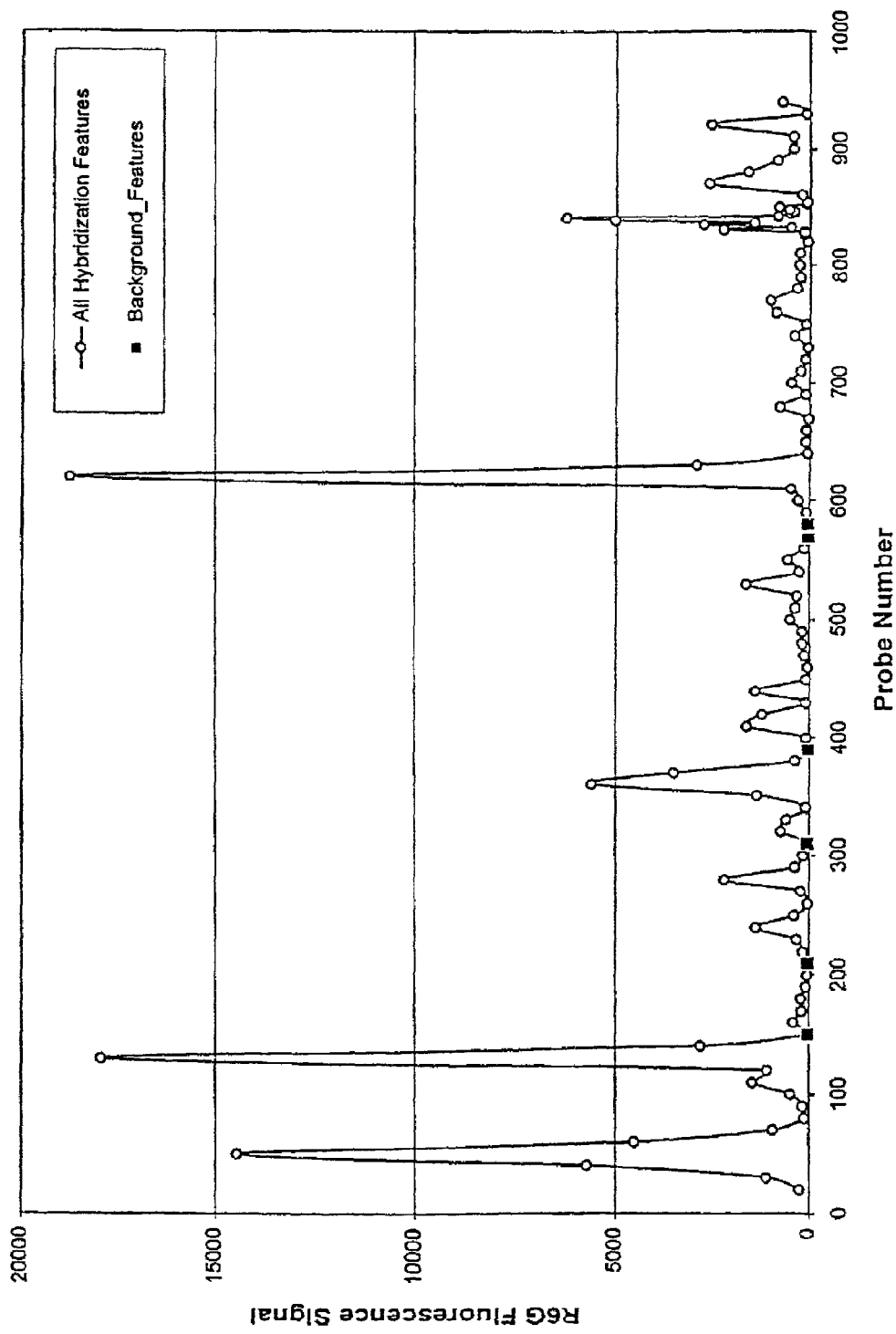
FIG. 1 illustrates the results of a hybridization assay, wherein empirically observed background probes (tabulated in Table 1) and specific hybridization probes were hybridized to rhodamine 6-G (R6G)-labeled G3PDH cRNA (SEQ ID NO: 1).

The practice of the present invention will employ, unless otherwise indicated, conventional techniques of chemistry, biochemistry, molecular biology, and medicine, including diagnostics, which are within the skill of the art. Such techniques are explained fully in the literature. See, e.g., *Solid-Phase Synthesis*, Blossey, E. C. and Neckers, D. C. Eds. 1975; Sambrook, Fritsch & Maniatis, *Molecular Cloning: A Laboratory Manual; DNA Cloning*, Vols. I and II (D. N. Glover ed.); *Oligonucleotide Synthesis* (M. J. Gait ed.); *Nucleic Acid Hybridization* (B. D. Hames & S. J. Higgins eds.); and the series, *Methods In Enzymology* (S. Colowick and N. Kaplan eds., Academic Press, Inc.); Beaucage and Carruthers, *Tetrahedron Lett.*, 22:1859–1862 (1981); Matteucci, et al, *J. Am. Chem. Soc.*, 103:3185 (1981); Letsinger, R. L. and Mahadevan, V., *J. Amer. Chem. Soc.*, 88:5319–5324.

All patents, patent applications, and publications mentioned herein, whether supra or infra, are hereby incorporated by reference in their entirety.

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a target analyte" includes a mixture of two or more such analytes, "a reagent" includes a mixture of two or more reagents, and the like.

Unless defined otherwise, all technical and scientific terms used herein have the same meaning as commonly understood by one of ordinary skill in the art to which the invention pertains. The following terms are intended to be defined as indicated below.

As used herein, the terms "hybridization," "hybridizing" and "binding" may be used interchangeably. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to the nucleotides in another sequence, the more stringent the conditions can be for hybridization and the more specific will be the binding of the two sequences. Increased stringency is achieved by elevating the temperature, increasing the ratio of co-solvents, lowering the salt concentration, and the like. Hybridization processes and conditions are described by Sambrook, J. et al., (*Molecular Cloning: A Laboratory Manual,* Cold Spring Harbor Laboratory Press, Cold Spring Harbor, $2^{nd}$ Ed., 1989, vol. 1-3). Conditions for hybridization typically include high ionic strength solution, controlled temperature, and the presence of carrier DNA and detergents and divalent cation chelators, all of which are well known in the art.

As used herein, the term "specific hybridization" refers to those occurrences in which a segment of an oligonucleotide probe preferentially hybridizes with a segment of a selected polynucleotide, as intended. The use of the term "hybridizes" is not meant to exclude non Watson-Crick base pairing.

As used herein, the term "nonspecific hybridization" refers to those occurrences in which a segment of an oligonucleotide probe does not preferentially hybridize to a segment of a selected, specific complementary first polynucleotide but also hybridizes to a second polynucleotide, triggering an erroneous result, i.e., giving rise to a situation where label may be detected in the absence of a the specific complementary polynucleotide (e.g. nucleotide sequence or a target molecule). The use of the term "hybridizes" is not meant to exclude non Watson-Crick base pairing.

As used herein, the term "nonspecific binding" is used to refer to those occurrences in which a polynucleotide binds to the solid support, or other assay component, through an interaction, which may be either direct or indirect, that does not involve hydrogen bonding to support-bound oligophosphodiesters.

A "nucleoside" has two components: a nitrogenous base and a pentose sugar. A "nucleotide" has 3 components: a nitrogenous base, a pentose sugar and a phosphate. (See, Lehninger A. L., et al., "*Principles of Biochemistry,*" 2nd Ed, Worth Publishers, (1993) p. 325).

As used herein, the term "oligophosphodiester," refers to polymeric molecules, including oligonucleotides, polynucleotides, modified nucleotides, modified nucleotidic units and abasic phosphodiesters, as described in, e.g., Example 5, infra.

As used herein, the terms "nucleic acid molecule," "oligonucleotide," "nucleotide sequence" and "polynucleotide" may be used interchangeably, and refer to nucleic acid molecules and polymers thereof, including conventional purine or pyrimidine bases as well as base analogs. Such molecules include without limitation nucleic acids, and fragments thereof, from any source in purified or unpurified form including DNA, double-stranded or single stranded (dsDNA and ssDNA), and RNA, including t-RNA, m-RNA, r-RNA, mitochondrial DNA and RNA, chloroplast DNA and RNA, DNA/RNA hybrids, or mixtures thereof, genes, chromosomes, plasmids, the genomes of biological materials such as microorganisms, e.g. bacteria, yeasts, viruses, viroids, molds, fungi, plants, animals, humans, and the like; polynucleotides containing an N- or a C-glycoside of a purine or pyrimidine base; other polymers containing non-nucleotidic backbones, for example, abasic phosphodiesters (as described in, e.g., Example 5, infra), polyamide (e.g., peptide nucleic acids (PNAs)) and polymorpholino (commercially available from the Anti-Virals, Inc., Corvallis, Oregon, as Neugene™ polymers), and other synthetic sequence-specific nucleic acid polymers providing that the polymers contain nucleobases in a configuration which allows for base pairing and base stacking, such as is found in DNA and RNA. The polynucleotide can be only a minor fraction of a complex mixture such as a biological sample. Also included are genes, such as hemoglobin gene for sickle-cell anemia, cystic fibrosis gene, oncogenes, cDNA, and the like.

The terms "polynucleotide" and "oligonucleotide," also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

Various techniques can be employed for preparing a polynucleotide. Such polynucleotides can be obtained by biological synthesis or by chemical synthesis. For short sequences (up to about 100 nucleotides), chemical synthesis is economical, provides a convenient way of incorporating low molecular weight compounds and/or modified bases during specific synthesis steps, and is very flexible in the choice of length and region of target polynucleotide binding sequence. Polynucleotides can be synthesized by standard methods such as those used in commercial automated nucleic acid synthesizers. Chemical synthesis of DNA on a suitably modified glass or resin can result in DNA covalently attached to the surface, potentially advantageous in washing and sample handling. For longer sequences standard replication methods employed in molecular biology can be used such as the use of M13 for single stranded DNA as described by Messing, J., *Methods Enzymol.,* 1983,101:20–78; or the use of polymerase chain reaction as described in U.S. Pat. Nos. 4,683,195; 4,683,202 and 4,965,188.

Other methods of polynucleotide synthesis include phosphotriester and phosphodiester methods (Narang, S. A. et al., *Meth. Enzymol.,* 1979, 68:90) and synthesis on a support (Beaucage, et al., *Tetrahedron Letters,* 1981, 22:1859–1862) as well as phosphoramidate techniques (Caruthers, M. H., et al., *Methods in Enzymology,* 1988, 154:287–314) and others described in *Synthesis and Applications of DNA and RNA* (Narang, S. A., editor, Academic Press, New York, 1987), and the references contained therein. Sequential addition of nucleotide phosphoramidites to surface-linked hydroxyl groups is described by T. Brown and Dorcas J. S. Brown in *Oligonucleotides and Analogues A Practical Approach,* F. Eckstein, editor, Oxford University Press, Oxford, pp 1–24 (1991). The chemical synthesis via a photolithographic method of spatially addressable arrays of oligonucleotides bound to glass surfaces is described by Pease, A. C. et al., *Proc. Nat. Aca. Sci.,* 1994, 91:5022–5026. Deposition of pre-synthesized oligonucleotides maybe accomplished by (1) covalent linkage of a chemically modified oligonucleotide (e.g. aliphatic primary amine) to the substrate surface bearing an amine-reactive group (e.g. aromatic isothiocyanate) as described in Guo Z. et al., *Nucleic Acids Res,* 1994, 22:5456–65, or (2) adsorption to a substrate surface coated with a positively charged polyelectrolyte (e.g. poly-L-lysine), followed by cross-linking to the surface chemically or photochemically (e.g. covalent stabilization via ultraviolet (UV) photo-crosslinking), as described in Schena, M. et al., *Science,* 1995, 270:467–70. Common deposition equipment used for forming arrays includes that described in Schena, M. et al.(cited above); Pease, A. C. et al., *Proc. Natl. Acad. Sci.,* 1994, 91:5022–6 and Blanchard, A. P. et al., *Biosensors & Bioelectronics,* 1996, 11:687–690.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, double stranded DNA (dsDNA) can be heated at 90–100° C. for a period of about 1 to 10 minutes to produce denatured material, while RNA produced via transcription from a ds-DNA template is already single stranded. A polynucleotide can have from about 5 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides.

As used herein, the term "modified nucleotide" refers to a naturally occurring or a synthetic unit in a nucleic acid polymer that contains modifications to the base, sugar and/or phosphate groups. The modified nucleotide can be produced by a chemical modification of a nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophore-labeled, and the like and also include phosphorothioate, phosphite, ring atom modified derivatives, and so forth.

Modified nucleosides or nucleotides will also include modifications on the sugar moiety, e.g., wherein one or more of the hydroxyl groups are replaced with halogen, aliphatic groups, or are functionalized as ethers, amines, or the like. Additionally, modified nucleotides will also include abasic phosphodiesters (as described in, e.g., Example 5, infra).

The term "nucleotidic unit" is intended to encompass nucleosides, nucleotides and modified nucleotides.

Furthermore, modifications to nucleotidic units include rearranging, appending, substituting for or otherwise altering functional groups on the purine and/or pyrimidine base which form hydrogen bonds to a respective complementary pyrimidine or purine. The resultant modified nucleotidic unit may form a base pair with other such modified nucleotidic units but not with A, T, C, G or U. Standard A-T and G-C base pairs form under conditions which allow the formation of hydrogen bonds between the $N^3$—H and $C^4$-oxy of thymidine and the $N^1$ and $C^6$—NH respectively, of adenosine and between the $C^2$-oxy, $N^3$ and $C^4$—$NH_2$, of cytidine and the $C^2$—$NH_2$, $N^1$—H and $C^6$-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine, 2'-deoxy-5-methyl-isocytidine, isoguanine nucleotides may be prepared by the method described in the art. See U.S. Pat. No. 5,681,702. Other such modified nucleotidic units which form unique base pairs have been described in Piccirilli et al. (1990) *Nature* 343:33–37 and Leach et al. (1992) *J. Am. Chem. Soc.* 114:3675–3683, or will be apparent to those of ordinary skill in the art.

As used herein, the term "abasic phosphodiester" refers to a polymer comprising DNA analogs formed from chemically modified precursors unable to form hydrogen bonds, or in which the nitrogenous bases are absent, or wherein the entire deoxyribose sugar-nitrogenous base moiety has been replaced by a polyether structure (for further details see, e.g., Example 5, infra). Such abasic phosphodiesters possess polyelectrolyte properties similar to normal DNA and yield a surface with similar nonspecific binding properties as surfaces bearing normal DNA strands.

The term "sample" refers to a sample derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). The sample may contain a single- or double-stranded nucleic acid molecule which includes a target nucleotide sequence and may be prepared for hybridization analysis by a variety of means, e.g., using proteinase K/SDS, chaotropic salts, or the like.

As used herein, the terms "target region" or "target nucleotide sequence" may be used interchangeably, and refers to a sequence of nucleotides to be identified, e.g., an analyte target nucleic acid, usually existing within a portion or all of a polynucleotide, usually a polynucleotide analyte. The identity of the target nucleotide sequence generally is known to an extent sufficient to allow preparation of various probe sequences hybridizable with the target nucleotide sequence. The term "target sequence" refers to a sequence with which a probe will form a stable hybrid under desired conditions. The target sequence generally contains from about 30 to 5,000 or more nucleotides, preferably about 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of detection and/or amplification of the target nucleotide sequence, where appropriate.

As used herein the term "xenogene" refers to non-mammalian genes, i.e. genes not derived from a mammalian genome, preferably a non-human genes. Xenogenes may be derived from any non-mammalian source, such as plants, yeasts, bacteria, virus, and the like.

A "hybridization probe", also termed a "normal probe" or a "real probe" herein, refers to a structure comprised of an nucleic acid, e.g., an oligonucleotide or polynucleotide, as defined above, which contains a nucleic acid sequence complementary to an analyte nucleic acid sequence present in the sample such that the hybridization probe will specifically hybridize to the target analyte nucleotide sequence under appropriate conditions, e.g., stringent hybridization conditions.

A "background probe" or a "negative control probe" is defined as a probe that closely mimics the nonspecific binding properties of hybridization or real probes, but which possesses no specific affinity for target nucleic acid sequences. In a preferred embodiment, the region of the array that contains background probe will locally and globally yield minimal signal levels. In certain embodiments, the length of the "hybridization" and "background" probes is generally from about 5 to about 500 nt, usually from about 5 to 250 nt, and more usually from about 5 to 100 nt, where in certain embodiments the length is generally from about 5 to about 50 nt, more preferably from about 10 to about 30 nt, and even more preferably from about 10 to about 25 nt. Additionally, the "hybridization" and "background" probes need not be the same length.

A "positive control probe" refers to a structure comprised of an oligonucleotide, as defined above, which contains a first nucleic acid sequence complementary to a second nucleic acid sequence of interest such that the positive control probe will specifically hybridize to the second nucleic acid sequence under appropriate conditions (for further details see, e.g., Examples 1, 2 and 6 infra).

As used herein, the term "feature" is defined as a set of plurality of probes, wherein the probes may be in solution or are bound to a surface. In preferred embodiments, the probes are bound to a surface, wherein each set of probes is arranged in a spaced-apart relation to each other at known locations. In more preferred embodiments, a feature is the region of the array that contain probes, the features are separated by regions devoid of probes, and each feature occurs at approximately known locations and is distinct from other features. The ratio of hybridization features to background features, as defined below, is 10,000 to 1, preferably 5,000 to 10, more preferably 2,000 to 50.

A "hybridization feature" is defined as a structure comprised of a plurality of hybridization probes that selectively hybridize to a detectably labeled target nucleotide sequence, wherein the target may be labeled prior to or after hybridization, preferably prior to hybridization, as defined above. In a preferred embodiment, a hybridization feature contains $3.1 \times 10^6$ to $6.3 \times 10^7$ hybridization probes, preferably $1.6 \times 10^7$ to $4.7 \times 10^7$, more preferably $2.8 \times 10^7$ to $3.5 \times 10^7$ hybridization probes.

A "background feature" is defined as a structure comprised of a plurality of background probes that do not selectively hybridize to the target nucleotide sequence, as defined above. A background feature is a feature that provides a signal during a hybridization assay that is made up of three components: (a) a feature substrate background component; (b) a probe background component; and (c) a non-specific binding component. In a preferred embodiment, a background feature is a region of an array that contains background probes covalently bound to the array-surface. In a preferred embodiment, a background feature contains $3.1 \times 10^6$ to $6.3 \times 10^7$ background probes, preferably $1.6 \times 10^7$ to $4.7 \times 10^7$, more preferably $2.8 \times 10^7$ to $3.5 \times 10^7$ background probes.

As used herein, a "standard-background feature" or "validated background feature" refers to a background feature comprising background probes which have been standardized/validated against the hybridization features according to the methods of the instant invention.

As used herein, a "test-background feature" refers to a background probe feature comprising non-standard background probes, i.e., new and/or unknown background probes that have not been standardized/validated. Test-background features are validated against the standard-background features and the hybridization features according to the methods of the instant invention. A test-background feature is validated if the signal from the test-background probe is as low as, or lower than signal from the standard-background. Additionally, the signal replicates between the test-background probe features of a given sequence should be as good as the signal replicates of the standard-background features. Monitoring the inter-feature % coefficient of variation (% CV) is an example of testing for accuracy of replication. The inter-feature % CV is calculated by dividing the inter-feature standard deviation by the inter-feature mean, and multiplying by 100.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention, and in most situations two sequences are sufficiently complementary when at least about 85% (preferably at least about 90%, and most preferably at least about 95%) of the nucleotides share base pair organization over a defined length of the molecule.

As used herein, the terms "reporter," "label" and "detectable label" refer to a molecule capable of detection, including, but not limited to, radioactive isotopes, fluorescers, chemiluminescers, enzymes, enzyme substrates, enzyme cofactors, enzyme inhibitors, dyes, metal ions, metal sols, ligands (e.g., biotin or haptens) and the like. The term "fluorescer" refers to a substance or a portion thereof which is capable of exhibiting fluorescence in the detectable range. The term "cofactor" is used broadly herein to include any molecular moiety which participates in an enzymatic reaction. Particular examples of labels which may be used under the invention include fluorescein, 5(6)-carboxyfluorescein, Cyanine 3 (Cy3), Cyanine 5 (Cy5), rhodamine, dansyl, umbelliferone, Texas red, luminol, NADPH, α,β-galactosidase and horseradish peroxidase.

The term "substrate" is used interchangeably herein with the terms "support" and "solid substrate," and denotes any solid support suitable for immobilizing one or more nucleic acid molecules as discussed further below.

As used herein, the term "array" is defined as a collection of separate probes each arranged in a spatially defined and a physically addressable manner. The number of probes or features that can be deposited on an array will largely be determined by the surface area of the substrate, the size of a feature and the spacing between features, wherein the array surface may or may not comprise a local background region represented by non-feature area. Generally, arrays can have densities of up to several hundred thousand or more features per cm$^2$, preferably about 2,500 to about 200,000 features/cm$^2$.

As used herein, the term "observed signal" is defined as the amount of signal generated from contacting the target nucleotide sequence with the features comprising oligophosphodiester probes, wherein the target nucleotide sequence may be labeled prior to or after hybridization, preferably prior to hybridization. The observed signal is a combination of the "real" or "hybridization" signal, i.e. the signal generated from the hybridization of the labeled target nucleotide sequence with the hybridization probes, and the background signal, as defined below.

As used herein, the term "background signal" is defined as the amount of signal generated from the background features, and the signal generated due to an undesirable interaction of various components used in a given assay, i.e. signal generated by entities other than due to hybridization of the analyte and the specified complementary probes, such as signal generated from (i) the reporter, i.e. a signal arising from the label itself when it is not attached to the target, such as a signal generated from a fluorescent dye used in labeling the target; (ii) the non-reporter, i.e. a signal generated from the substrate or other assay components, and (iii) signal generated due to non-specific binding of probes to labeled entities other than their specific target molecules, i.e. binding not related to hybridization of the analyte and the complementary probes.

As used herein, the term "local background signal" is defined as the signal generated from the portion of the array outside of the probe feature area, generally, the area immediately adjacent to a given feature.

As used herein, the term "global background signal" is determined by calculating either the minimum or the average value of all the local background signals from an entire array.

As used herein, the term "non-reporter signal" is defined as a signal generated from the substrate or other assay components, not from the reporter.

As used herein, the term "Lowest Limit of Detection (LLD)" is defined as the lowest concentration of analyte that yields a signal which is statistically significantly greater than the background signal. Generally, the signal will be greater than the sum of the background signal and the noise of the background signal measurement. This sum of background signal and noise is referred to as the threshold. Thus, LLD is an important analytic method performance parameter that is particularly sensitive to background measurement methods. Often, two standard deviations of the sampled background distribution (2σ) is used to track noise, if the noise is normally distributed. Alternatively, a composite estimation of noise that tracks both observed signal noise and background signal noise is calculated. If the estimation of noise uses the sum of the background signal and two standard deviations as a threshold, the resulting net signal which is calculated will have a confidence of 95% of being different from the background.

As used herein, the term "pixel signal variation" is defined as a method of calculating noise of a feature or noise of the local background. The signal from a feature or signal from a local background region is reported as a statistically relevant value (e.g., average or median) of all the individual pixel signals within that feature or local background region. The standard deviation of the pixel signals within a feature or local background region can be used to characterize the pixel statistics of that feature or region. The percent coefficient of variation (% CV) is calculated by dividing the intra-feature standard deviation by the intra-feature mean, and multiplying by 100.

An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

DESCRIPTION OF THE SPECIFIC EMBODIMENTS

Nucleic acid arrays that have background features and methods for using the same are provided. The subject nucleic acid arrays include both hybridization features and background features, where the background features provide a background signal in a hybridization assay that is made up of a feature substrate component, a nucleic acid probe component and a nucleic acid probe non-specific binding component. In practicing the subject methods, the arrays are contacted with a sample and signals are observed for both hybridization features and background features. The background feature signal is then subtracted from the hybridization feature signal to obtain a background corrected hybridization feature signal that is employed as the output of the assay, e.g., to determine the presence of or amount of the analyte target nucleic acid in the sample. Also provided are kits for use in practicing the subject methods.

Before describing the present invention in detail, it is to be understood that this invention is not limited to particular formulations or process parameters as such may, of course, vary. It is also to be understood that the terminology and examples used herein are for the purpose of describing particular embodiments of the invention only, and are not intended to be limiting.

Although a number of compositions and methods similar or equivalent to those described herein can be used in the practice of the present invention, the preferred materials and methods are described.

In further describing the subject invention, the subject arrays are described first in greater detail, followed by a review of methods of using the subject arrays and kits for use in practicing the subject methods.

Arrays

The arrays of the present invention are made up of a substrates having a surface on which are immobilized at least one hybridization feature (made up of polymeric hybridization probes) and at least one background feature (made up of background probes). By immobilized is meant that the hybridization and background polymeric probes that make up the hybridization and background features, respectively, are stably associated with the surface of the substrate during hybridization and washing conditions, described in greater detail below. In many embodiments, the polymeric probes are covalently bonded to the substrate surface.

As indicated above, probes for use in the subject invention include "hybridization" or "normal" or "real" probes; "background" or "negative control" probes and "positive control" probes. A hybridization probe or a real probe that binds to a target molecule is preferably one which binds to that target with high specificity. Preferably, the probe is covalently attached to the array surface. A probe-nucleic acid molecule will be specific for a nucleic acid target molecule with a base sequence complementary to the probe nucleic acid molecule. The probe-nucleic acid molecule hybridizes to the target molecule under stringent hybridization conditions.

As explained above, a variety of nucleic acid molecules can be used to form the hybridization probes. See, generally, Wetmur, J. (1991) *Crit Rev Biochem and Mol Bio* 26:227. In particular, modified nucleic acids, e.g., oligonucleotides, can be used to increase selectivity and sensitivity of the probes. Such modified nucleic acids are well known in the art and described in e.g., Chollet et al. (1988) *Nucleic Acids Res* 16:305; Potapov et al. (1996) *Pure & Appl. Chem* 68:1315; Soloman et al. (1993) *J Org Chem* 58:2232; Prosnyak et al. (1994) *Genomics* 21:490; Lin et al. (1991) *Nucleosides & Nucleotides* 10:675. For example, substitution of 2-aminoadenine for adenine, or substitution of 5-methylycytocine for cytosine can increase duplex stability. Prosnyak et al, supra. In addition, nucleic acid probes containing both types of modified bases have increased duplex stability relative to unmodified analogs. Furthermore, substitution of 2-aminoadenine (2-AA) for adenine creates an additional hydrogen bond in the Watson-Crick base pair (Chollet et al., supra), and oligonucleotide probes containing 2-AA show increased selectivity and hybridization to target DNA. In this regard, 2-AA is used only as a substitute for adenine, and binds in a manner similar to the natural base. Other examples of modified nucleic acids include the use of a base pair wherein a modified pyridone or quinolone base pairs with 2-aminopurine (Solomon et al., supra), and the use of deoxycitidine derivatives in triplex formation (Huang et al. (1996) *Nucleic Acids Res.* 14:2606).

Hybridization probes for use with the present methods may be assembled using a combination of solid phase direct oligophosphodiester synthesis, enzymatic ligation methods, and solution phase chemical synthesis. Various methods for synthesizing probes are well known in the art. For example, it is a matter of routine to synthesize desired nucleic acid probes using conventional nucleotide phosphoramidite chemistry and instruments available from, e.g., Applied Biosystems, Inc., (Foster City, Calif.), Dupont (Wilmington, Del.), or Milligen (Bedford Mass.). Thus, all chemical syntheses of oligophosphodiesters can be performed on an automatic DNA synthesizer, such as a Perkin Elmer/Applied Biosystems Division model 380 B. For example, phosphoramidite chemistry of the β-cyanoethyl type can be used including 5'-phosphorylation which employs PHOSTEL™ reagent (DMT—O—$CH_2$—$CH_2$—($SO_2$)—$CH_2$—$CH_2$—O—P(N(iPr)$_2$)(—O—$CH_2CH_2CN$) wherein DMT is dimethoxytrityl and iPr is isopropyl.

Hybridization probes can be provided that hybridize with a variety of nucleic acid targets, such as viral, prokaryotic, and eukaryotic targets. The target may be a DNA target such as a gene (e.g., oncogene), control element (e.g., promoter, repressor, or enhancer), or sequence coding for ribosomal RNA, transfer RNA, mRNA, or RNase P. The target may be a viral genome or complementary copy thereof. Additionally, the target may be a "nucleic acid amplification product," e.g., a nucleic acid molecule, either DNA or RNA, resulting from the introduction of an enzyme or enzymes into the cell, wherein such enzymes make a nucleic acid molecule complementary to one already present in the cell. See, e.g, O. Bagasra et al. (1992) *The New England Journal of Medicine* 326:1385–1391.

A background probe or a negative control probe, unlike the hybridization probe, is a probe that binds to target molecules only minimally and is preferably one that closely mimics the nonspecific binding properties and the non-reporter signal generation properties of the hybridization probe. In the case of surface-bound probes, the surface of background probe features also preferably mimics the surface of hybridization features as to their non-reporter signal generation and their non-specific binding of reporter and target. In other words, the background probes of the subject invention are those probes that, when present as a feature of an array, provide a background signal during a hybridization assay that is made up of three background components: (1) the feature substrate component; (2) the probe molecule component and (3) the nonspecific binding component of the probe molecule. Background probes possess no specific affinity for target nucleic acid sequences. Preferably, a background probe is covalently attached to the array surface (background probe feature). Background probes of the invention include, but are not limited to, empirically observed probes; probes that form stable intramolecular structures, such as hairpins and pseudo-half knots; short probes; probes comprising reverse polarity nucleotide analogs; probes comprising abasic phosphodiesters or modified nucleotidic units, and the like.

Examples of empirically observed inactive probes are shown in Table 1, infra. In particular, these probes have been observed to bind their complementary targets very minimally, yielding minimal signal levels in hybridization assays and as such are useful as background probes in the methods of the subject invention. The probes shown in Table 1 are from sequences originally designed to bind human G3PDH (SEQ ID NO: 1) and P53 (SEQ ID NO: 4) targets. When the probes were allowed to hybridize to their complementary specific targets, very poor binding was observed. Subsequently, other purified targets, as well as complex pool RNA, were also observed to bind very poorly to these probes.

Examples of probes including intramolecular hairpin structures are shown in Table 2, infra. These probes possess nonspecific binding properties similar to those of hybridization probes. Such probes are single-stranded oligonucleotides which include regions of internal complementarity such that double-stranded loops are formed by base-pairing between sequences in the strand which are complementary. In a preferred embodiment, such probes are single-stranded oligonucleotides which include regions of internal complementarity such that double-stranded loops are formed by base-pairing between sequences in the strand which are complementary and opposite in polarity.

Examples of short probes are shown in Table 5, infra (for further details, see, e.g., Example 4, infra). Other useful background probes include those that comprise reverse polarity nucleotide analogs, i.e. probes wherein the deoxyribose sugar-nitrogenous base backbone comprises nucleotides attached such that they are in opposite polarity as compared to the adjacent nucleotides. These nucleotides are capable of forming oligonucleotides with alternating {3'→3'} and {5'→5'} phosphodiester linkages, instead of the naturally occurring {3'→5'} phosphodiester linkages. (See, e.g., U.S. Pat. Nos. 5,399,676; 5,527,899 and 5,721,218 and Koga, M. et al. (1991) *J. Org. Chem.* 56:3757–3759).

Generally, the probe comprises about 1 to about 50 reverse polarity nucleotide analogs, more preferably about 2 to about 25 reverse polarity nucleotide analogs, and even more preferably about 5 to about 10 reverse polarity nucleotide analogs. Such probes are synthesized using techniques well known in the art. (See, e.g., Koga, M. et al.).

Figure 6:
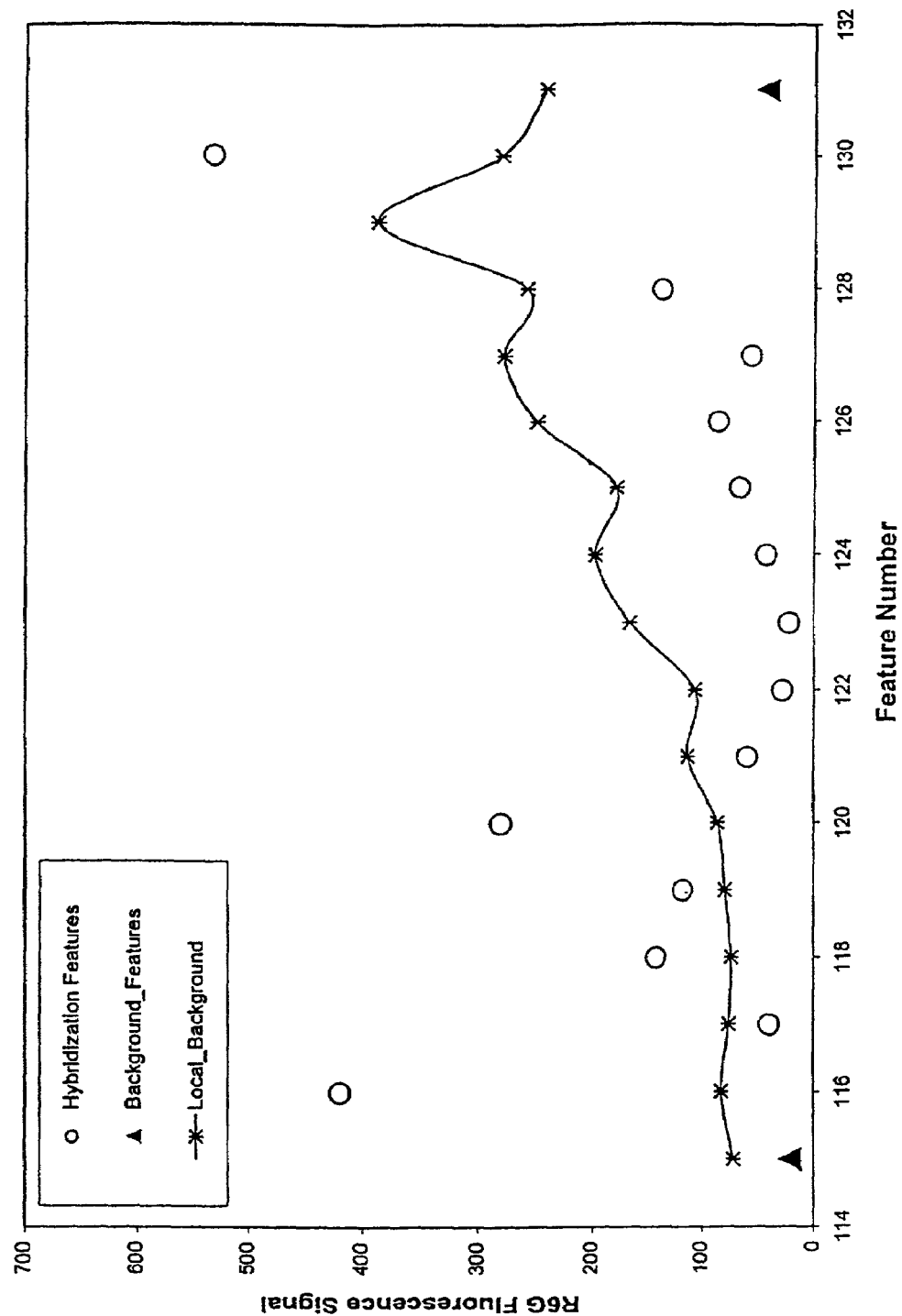
FIG. 6 shows the signal from a region of an array, illustrating the signal from background features, hybridization features and local background. As observed in the figure, the signal from the background features is much less than the surrounding local background, yielding "negative features."

In another embodiment, the background probe comprises abasic phosphodiesters or modified nucleotidic units, which minimize nonspecific hybridization and nonspecific binding. Examples of abasic phosphodiesters include, but are not limited to, analogs of modified DNA, wherein the substituents are replaced, or wherein the deoxyribose sugar-phosphodiester backbone with nitrogenous bases is substituted with a sugar-phosphodiester backbone without nitrogenous bases, or a backbone comprising polyether, and the like. Examples of phosphoramidite monomers used to synthesize an abasic phosphodiester, using standard chemical synthetic techniques, are illustrated in FIG. 6 and are commercially available (Glen Research, Sterling, Va.). For example, in structure I, the nitrogenous base in the deoxyribose sugar ring is replaced with hydrogen. In structure II, the deoxyribose sugar ring is replaced by a triethylene glycol unit. Analogs of Structure II are obtained by replacing triethylene glycol with monoethyleneglycol and hexaethyleneglycol. Compounds of Structures I and II are commercially available (Glen Research, Sterling, Va.). Preferably, these oligo-phosphodiesters are prepared using standard phosphoramidite-based synthetic methods.

In certain preferred embodiments, the background features present on the subject arrays are those background features that test positive as background features in a two-color self-self hybridization assay. In other words, the background features present on the subject arrays are ones that have been identified as adequate background features in a two-color self-self hybridization assay.

In a two-color self-selfhybridization assay, a candidate background feature is tested for its ability to serve as a background feature for a given array of nucleic acids. In this assay, the given array of nucleic acids with which the candidate background feature is intended or contemplated to be employed is provided, where the array includes the candidate background feature. For example, in testing a candidate background feature for an array of hybridization features each made up of nucleic acid probes that are 60 nt in length, i.e., a 60-mer array, an array is prepared having a plurality of different 60 nt long hybridization features made up of 60 nt long hybridization probes and a candidate background feature, where the candidate background feature may be made up of background polymers, e.g., nucleic acids, that are 60 nt length, or shorter or longer, as described above.

Next, two different target nucleic acid populations are produced, i.e., a first and second target nucleic acid population are provided, e.g., obtained from a commercial source or produced/synthesized from starting materials. The first and second target nucleic acid populations are substantially identical in terms of nucleic acid profile, i.e., that are substantially the same, and preferably identical, in terms of the different types, and amount of each type, of target nucleic acid that is in the population. For example, where the first target nucleic acid population has 100 different target nucleic acids each present in amount X, the second target nucleic acid population also preferably has 100 different target nucleic acids each present in an amount X. The difference between the two target populations is the manner in which they are labeled. Specifically, the first target population is labeled with a first label and the second target population is labeled with a second label, where the first and second labels are distinguishable from each other. In many embodiments, the first and second labels are distinguishable fluorescent labels, e.g., red and green labels. For an example of methods of producing two distinguishably labeled target nucleic acid populations, see e.g. U.S. Pat. No. 5,800,992, the disclosure of which is herein incorporated by reference.

The target nucleic acids present in each of the populations are made up of target nucleic acid known to hybridize to the various hybridization features on the array. For example, where the array has 100 different hybridization features or hybridization probes, each target nucleic acid may include 100 different types of target nucleic acids, one for each feature.

The first and second target nucleic acid populations are then contacted with the array under hybridization, e.g., stringent hybridization, conditions. Following removal of unbound target, the signals of both labels are detected for each of the hybridization features of the array. The signal detected from the candidate background feature for each label is also detected. The resultant signals of the different labels are then background corrected by subtracting from the detected signal for each hybridization feature for each label the corresponding background feature signal for that label obtained from the candidate background feature. This process yields background corrected signals for each hybridization feature of the array for each of the two labels, where the background corrected signals are corrected with the background signal obtained from the candidate background feature.

The two different background corrected signals (i.e., label 1 signal and label 2 signal) for each hybridization feature on the array are then compared to identify differences in the signal obtained for each label for that feature, i.e., to identify any variance in signal. For a substantial majority of the hybridization features, any variance in background corrected signals for the two labels should be minimal for the background feature to be determined to be a suitable background feature for the array. By substantial majority is meant at least about 60 number %, usually at least about 75 number %, and more usually at least about 90 number %. Minimal variance means that the magnitude of any variation in signal does not exceed about 33%, usually does not exceed about 25% and more usually does not exceed about 10%, where in many embodiments the variance observed is preferably much less, e.g., less than 5%, preferably less than 2.5%.

The two different signals for each feature on the array may be compared using any convenient protocol. For example, the test background feature background corrected signals for each hybridization feature may be graphically compared. In graphically comparing the signals, for each feature the background corrected signal obtained using the first label is plotted against the background signal obtained for that feature from the second label. For example, the signal for each feature obtained using the first label is plotted on the Y axis and the signal obtained for each feature using the second label is plotted on the X axis. See e.g., the experimental section supra.

The resultant line yielded by the plot of the two background corrected signals for each feature is then used to determine the suitability of the candidate background feature for use as a background feature on an array, i.e., an array that is substantially the same as, if not identical to, the array used in the two-color self-self hybridization assay. For a candidate background feature to be determined suitable as a background feature, i.e., to test positive in the two-color self-selfhybridization assay, the resultant line (i.e. correlation line) yielded by the plot should be a substantially straight line, if not a straight line, with any noise in the lower signal intensity domain being symmetric about the plot or correlation line yielded from the plot of the background corrected signals.

The above described two-color self-self hybridization assay is employed to identify suitable background features for a given array. This assay can be employed to identify suitable background features for a large number of different types of arrays, where the arrays may be oligonucleotide arrays or polynucleotide arrays, e.g., cDNA arrays, etc. The Experimental section, below, provides a representative assay employed to identify suitable background features for a 60 mer array. The suitable background features for 60-mer arrays identified in this assay are provided in Table 10.

The subject arrays may be produced using any convenient protocol. Various methods for forming arrays from pre-formed probes described above, or methods for generating the array using synthesis techniques to produce the probes in situ, are generally known in the art. See, for example, Southern, U.S. Pat. No.5,700,637; Pirrung, et al., U.S. Pat. No.5,143,854; PCT International Publication No. WO 92/10092; and, Fodor, et al. (1991) *Science* 251:767–777.

For example, probes can either be synthesized directly on the solid support or substrate to be used in the hybridization reaction or attached to the substrate after they are made. A variety of solid supports or substrates may be used to practice the method of the invention. In a preferred embodiment the substrate comprises a porous or non-porous water insoluble material. The substrate may be selected from a wide variety of materials including, but not limited to, inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyamides, polyacrylamide, polyacrylate, polymethacrylate, polyesters, polyolefins, polyethylene, polytetrafluoro-ethylene, polypropylene, poly (4-methylbutene), polystyrene, poly(ethylene terephthalate), nylon, poly(vinyl butyrate), cross linked dextran, agarose, etc.; either used by themselves or in conjunction with other materials; fused silica (e.g., glass), bioglass, silicon chips, ceramics, metals, and the like. For example, substrates include polystyrene, to which short oligophosphodiesters, e.g., oligonucleotides ranging from about 5 to about 50 nucleotides in length, may readily be covalently attached (Letsinger et al. (1975) *Nucl. Acids Res.* 2:773–786), as well as polyacrylamide (Gait etal. (1982) *Nucl. Acids Res.* 10:6243–6254), silica (Caruthers et al. (1980) *Tetrahedron Letters* 21:719–722), and controlled-pore glass (Sproat et al. (1983) *Tetrahedron Letters* 24:5771–5774). Natural or synthetic assemblies such as liposomes, phospholipid vesicles, and cells can also be employed as substrates. Additionally, the substrate can be hydrophilic or capable of being rendered hydrophilic.

Suitable substrates may exist, for example, as gels, sheets, tubing, spheres, containers, pads, slices, films, plates, slides, strips, plates, disks, rods, particles, beads, etc. The substrate is preferably flat, but may take on alternative surface configurations. The substrate can be a flat glass substrate, such as a conventional microscope glass slide, a cover slip and the like. Common substrates used for the arrays of probes are surface-derivatized glass or silica, or polymer membrane surfaces, as described in Guo, Z. et al. (cited above) and Maskos, U. et al., *Nucleic Acids Res,* 1992,20:1679–84 and Southern, E. M. et al., *Nucleic acids Res,* 1994, 22:1368–73.

Immobilization of the probe to a suitable substrate may be performed using conventional techniques. See, e.g., Letsinger et al. (1975) *Nucl. Acids Res.* 2:773–786; Pease, A. C. et al., *Proc. Nat. Acad. Sci. USA,* 1994, 91:5022–5026. and "Oligonucleotide Synthesis, a Practical Approach," Gait, M. J. (ed.), Oxford, England: IRL Press (1984). The surface of a substrate may be treated with an organosilane coupling agent to functionalize the surface. One exemplary organosilane coupling agent is represented by the formula $R_nSiY_{(4-n)}$ wherein: Y represents a hydrolyzable group, e.g., alkoxy, typically lower alkoxy, acyloxy, lower acyloxy, amine, halogen, typically chlorine, or the like; R represents a nonhydrolyzable organic radical that possesses a functionality which enables the coupling agent to bond with organic resins and polymers; and n is 1, 2 or 3, usually 1. One example of such an organosilane coupling agent is 3-glycidoxypropyltrimethoxysilane ("GOPS"), the coupling chemistry of which is well-known in the art. See, e.g., Arkins, "Silane Coupling Agent Chemistry," *Petrarch Systems Register and Review,* Eds. Anderson et al. (1987). Other examples of organosilane coupling agents are (γ-aminopropyl)triethoxysilane and (γ-aminopropyl)trimethoxysilane. Still other suitable coupling agents are well known to those skilled in the art. Thus, once the organosilane coupling agent has been covalently attached to the support surface, the agent may be derivatized, if necessary, to provide for surface functional groups. In this manner, support surfaces may be coated with functional groups such as amino, carboxyl, hydroxyl, epoxy, aldehyde and the like.

Use of the above functionalized coatings on a solid support provides a means for selectively attaching oligophosphodiesters to the support. Thus, an oligonucleotide probe formed as described above may be provided with a 5'-terminal amino group which can be reacted to form an amide bond with a surface carboxyl using carbodiimide coupling agents. 5' attachment of the oligonucleotide may also be effected using surface hydroxyl groups activated with cyanogen bromide to react with 5'-terminal amino groups. 3'-terminal attachment of an oligonucleotide probe may be effected using, for example, a hydroxyl or protected hydroxyl surface functionality.

An array for use with the present invention will generally be constructed such that the ratio of hybridization features to background features is between about 10,000 to about 1, preferably between about 5,000 to 10, more preferably between about 2,000 to 50.

In certain embodiments, the arrays include 2 or more different background features, where any two background features are considered to be different if the sequence of the background probes that make up each of the any two background features differs from each other. In many embodiments, the number of different background features on the array ranges from 1 to 50, usually from about 2 to 25.

Methods

The subject nucleic acid arrays described above find use in hybridization assays in which a sample is assayed for the presence, either qualitatively or quantitatively, of one or more analyte target nucleic acids. In general, the array is reacted with a sample suspected of including the analyte target nucleotide sequence, wherein the target nucleotide sequence is labeled, and further wherein the target nucleotide sequence may be labeled prior to or after hybridization, preferably prior to hybridization. The resulting hybridization mixture is then analyzed to detect (i) the observed signal, i.e. the amount of signal generated from contacting the target nucleotide sequence with the features comprising nucleic acid, e.g., oligophosphodiester probes, and (ii) the amount of background signal generated from a variety of sources of background signal, including non-specific binding of the labeled target nucleotide sequence to the background probes. Finally, the presence and/or amount of the target nucleotide sequence in the analyte is determined by subtracting the background signal from the observed signal of the labeled target nucleotide sequence with the hybridization probes. Each of these steps is now described separately in greater detail.

In practicing the subject methods, the array is contacted with an fluid sample suspected of containing a target nucleotide sequence and incubated under suitable hybridization conditions. Hybridization generally takes from about 30 minutes to about 24 hours, and occurs at the highest specificity approximately 10–25° C. below the temperature ($T_m$) at which the nucleotide hybrid is 50% melted. The $T_m$ for a particular hybridization pair will vary with the length and nature of the nucleotides and may be readily determined by those of ordinary skill in the art.

Generally, a nucleic acid molecule is capable of hybridizing selectively or specifically to a target sequence under moderately stringent hybridization conditions. In the context of the present invention, moderately stringent hybridization conditions generally allow detection of a target nucleic acid sequence of at least 14 nucleotides in length having at least approximately 70% sequence identity with the sequence of the selected nucleic acid probe. In another embodiment, such selective hybridization is performed under stringent hybridization conditions. Stringent hybridization conditions allow detection of target nucleic acid sequences of at least 14 nucleotides in length having a sequence identity of greater than 90% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach,* editors B. D. Hames and S. J. Higgins, (1985) Oxford; Washington, D.C.; IRL Press). In many embodiments, the conditions employed are stringent, as defined above.

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is well within the skill of a person of ordinary skill in the art (see, for example, Sambrook, et al., *Molecular Cloning: A Laboratory Manual,* Second Edition, (1989) Cold Spring Harbor, N.Y.).

In general, hybridization is carried out in a buffered aqueous medium typically formulated with a salt buffer, detergents, nuclease inhibitors and chelating agents, using techniques well-known to those skilled in the art. Such formulations may be selected to preclude significant non-specific binding of nucleotides with the support-bound array. Various solvents may be added to the medium such as formamide, dimethylformamide and dimethylsulfoxide, and the stringency of the hybridization medium may be controlled by temperature, pH, salt concentration, solvent system, or the like. Defining appropriate hybridization conditions is within the skill of the art. See, e.g., Sambrook, Fritsch & Maniatis, *Molecular Cloning: A Laboratory Manual,* Second Edition (1989).

At some point prior to the detection step, described below, any target analyte nucleic acid present in the initial sample contacted with the array is labeled with a detectable label. Labeling can occur either prior to or following contact with the array. In other words, the nucleic acids present in the fluid sample contacted with the array may be labeled prior to or after contact, e.g., hybridization, with the array. In some embodiments, the sample nucleic acids (including the analyte target nucleotide sequence(s) if present in the sample) are directly labeled with a detectable label, wherein the label may be covalently or non-covalently attached to the nucleic acids of the sample. For example, the nucleic acids, including the target nucleotide sequence, may be labeled with biotin, exposed to hybridization conditions, wherein the labeled target nucleotide sequence binds to an avidin-label or an avidin-generating species. (Also see Example 1, infra). In an alternative embodiment, the target nucleotide sequence is indirectly labeled with a detectable label, wherein the label may be covalently or non-covalently attached to the target nucleotide sequence. For example, the label may be non-covalently attached to a linker group, which in turn is (i) covalently attached to the target nucleotide sequence, or (ii) comprises a sequence which is complementary to the target nucleotide sequence. In another example, the probes may be extended, after hybridization, using chain-extension technology or sandwich-assay technology to generate a detectable signal (see, e.g., U.S. Pat. No. 5,200,314). Generally, such detectable labels include, but are not limited to, radioactive isotopes, fluorescers, chemiluminescers, enzymes, enzyme substrates, enzyme cofactors, enzyme inhibitors, dyes, metal ions, metal sols, ligands (e.g., biotin or haptens) and the like.

In one embodiment, the label is a fluorescent compound, i.e., capable of emitting radiation (visible or invisible) upon stimulation by radiation of a wavelength different from that of the emitted radiation, or through other manners of excitation, e.g. chemical or non-radiative energy transfer. The label may be a fluorescent dye. Preferably, a target with a fluorescent label includes a fluorescent group covalently attached to a nucleic acid molecule capable of binding specifically to the complementary probe nucleotide sequence. Fluorescent groups useful as labels in this invention include, but are not limited to, fluorescein (or FITC), Texas Red, coumarin, rhodamine, rhodamine derivatives, phycoerythrin, Perci-P, 4-methylumbelliferyl phosphate, resorufin, 7-diethylamino coumarin-3- carboxylic acid succinimidyl ester, and the like. Fluorescent groups having near infrared fluorescence include, but are not limited to, indocyanine green [CAS 3599–32–4], copper phthalocyanine [CAS 147-14-8], 3,3'-diethyl-19,11:15,17-dienopentylene-2,2'-thiapentacarbocyanine, and the like.

Additionally, the label may be an aromatic compound (having one or more benzene or heteroaromatic rings or-polycyclic aromatic or heteroaromatic structures). Labels for use in the present invention may also include chemiluminescent groups such as, but are not limited to, isoluminol (4-aminophthalhydrazide), and the like. In an additional embodiment, the label is a protein or an enzyme. In a preferred embodiment, the enzyme is capable of catalyzing a reaction that produces a detectably labeled product.

Methods for attaching labels to target nucleotide sequence are similar to the methods for attaching labels to probes which are well known in the art. Enzo Biochemical (New York, N.Y.), Clontech Laboratories, Inc. (Palo Alto, Calif.)

and Ambion, Inc. (Austin, Tex.) (see Example 1, infra) have described and commercialized polynucleotide-labeling techniques. (See e.g., U.S. Pat. Nos. 5,260,433; 5,241,060; 4,994,373; 5,401,837 and 5,141,183). For example, a primary amine can be attached to a 3' oligo terminus or a 5' oligo terminus. The amines can be reacted to various haptens using conventional activation and linking chemistries. International Publication Nos. WO 92/10505 and WO 92/11388 teach methods for labeling polynucleotides at their 5' and 3' ends, respectively. According to one known method for labeling an oligonucleotide, a label-phosphoramidite reagent is prepared and used to add the label to the oligonucleotide during its synthesis. See, for example, N. T. Thuong et al. (1988) Tet. Letters 29:5905–5908. Preferably, target polynucleotides are labeled multiple times by inclusion of labeled nucleotides during target oligonucleotide synthesis.

Following hybridization and labeling, as described above, the label is detected using calorimetric, fluorimetric, chemiluminescent or bioluminescent means. Fluorescent labels are detected by allowing the fluorescent molecule to absorb energy and then emit some of the absorbed energy; the emitted energy is then detected using fluorimetric means. Preferably, the fluorescent dye is excitable by inexpensive commercially available lasers (e.g. HeNe, Micro Green, or solid state), has a quantum yield greater than 10%, exhibits low photo-bleaching and can be easily incorporated into target. In a preferred embodiment, when the target is labeled with R6G (Rhodamine-6-G), the label is detected by exciting at about 480 nm to about 550 nm, preferably at about 524 mn, and measuring light emitted at wavelengths at about 530 nm to about 610 nm, preferably at about 557 nm. Generally, reasonable precautions are taken to minimize the concentration of species that absorb the excitation energy and emit in the detection range.

Chemiluminescent label groups are detected by allowing them to enter into a reaction, e.g., an enzymatic reaction, that results in the emission of energy in the form of light. Other labels, e.g. biotin, may be detected because they can bind to groups such as streptavidin which are bound, directly or indirectly to enzymes, e.g. (alkaline phosphatase or horseradish peroxidase) that can catalyze a detectable reaction.

The signals detected from the hybridization features are then background corrected with signals obtained from the hybridization features in order to obtain background corrected signals for each hybridization feature of interest on the array. The background corrected signals are generally obtained by subtracting the signal of a background feature, or the average signal from a plurality of background features.

The resultant background corrected signals for each of the hybridization features are then employed to detect the presence of the analyte of interest in the assayed sample, either qualitatively or quantitatively.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. The data may be transmitted to the remote location for further evaluation and/or use. Any convenient telecommunications means may be employed for transmitting the data, e.g., facsimile, modem, internet, etc.

Utility

The subject arrays find use in a variety applications, where such applications are generally analyte detection applications in which the presence of a particular analyte nucleic acid in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc, as described above. The presence of the analyte in the sample is then deduced from the detection of binding complexes on the substrate surface. Included within this method is a background correction step, in which signal produced by background features on the array is subtracted from signals produced by hybridization features of the array.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; WO 95/21265; WO 96/31622; WO 97/10365; WO 97/27317; EP 373 203; and EP 785 280; the disclosures of which are herein incorporated by reference.

As such, the methods described herein are useful in conjunction with any number of assay formats, such as in situ hybridization assays, Southern blotting, Northern blotting, dot blots and PCR reactions, including assays wherein the probes may be in solution or are bound to a surface.

Kits

Finally, kits for use in analyte detection assays are provided. The subject kits at least include the arrays of the subject invention. The kits may further include one or more additional components necessary for carrying out the analyte detection assay, such as sample preparation reagents, buffers, labels, and the like. As such, the kits may include one or more containers such as vials or bottles, with each container containing a separate component for the assay, such as an array, and reagents for carrying out nucleic acid hybridization assays according to the invention. Thus, the kit will comprise in packaged combination, an array according to the subject invention, wherein the array comprises hybridization probes that selectively hybridize to the detectably labeled target nucleotide sequence, and background probes that do not selectively hybridize to the target nucleotide sequence. The kit may also include a denaturation reagent for denaturing the analyte, hybridization buffers, wash solutions, enzyme substrates, negative and positive controls and written instructions for carrying out the assay. In addition, the kits typically further include instructions for how practice the subject analyte detection methods according to the subject invention, where these instructions are generally present on at least one of a package insert and the package of the kit.

The following examples are illustrative in nature, and are not intended to limit the scope of the present invention in any manner.

EXPERIMENTAL

EXAMPLE 1

Empirically Observed Inactive Probes

In the process of trying to discover and validate probes for arrays that are sensitive to finding their targets, several probes that do not hybridize against their specific target were discovered. This example used in situ oligonucleotide probe arrays and R6G-labeled cRNA of the G3PDH gene (human glyceraldehyde-3-phosphate dehydrogenase gene), wherein the target polynucleotide (SEQ ID NO: 1) is the Watson-Crick complement of the mRNA. The probes in each feature used the sense-strand sequence of the G3PDH gene as input. The design produced 25-mer probes that were spaced at 10 base intervals along the sequence, generating an array of 200 features which were regularly spaced across the entire G3PDH sequence.

The oligonucleotide probes can be synthesized in situ, using standard methods of sequential phosphoramidite addition. Alternatively, the oligonucleotide probes can be synthesized by conventional chemosynthetic techniques (e.g. phosphoramidite chemistry) or by biosynthetic techniques (e.g. polymerase chain reaction "PCR"), printed onto the array surface, and covalently linked to that surface. See Brown T. et al., *Oligonucleotides and Analogues A Practical Approach,* and Schena M. et al., *Science.* The probe ingredients are printed or added to the feature locations of the substrate surface preferably using a modified thermal or piezoelectric inkjet-printing device. Pre-synthesized probes or probe compositions are printed, using the preferred printing device, on any of the array substrates mentioned previously, and preferably, are immobilized on the substrate using a poly-L-lysine coated substrate surface. For the purposes of the invention, the array of probes may be fabricated using conventional photolithography techniques as well. See, for example, Pease A. C. et al., *Proc. Natl. Acad. Sci. USA.*

R6G-labeling of G3PDH cRNA (SEQ ID NO: 1) was accomplished by the following method. DNA templates containing T-7 RNA polymerase promoter sites were transcribed into RNA using Ambion's MAXIscript In Vitro Transcription Kit (Ambion, Inc., Austin, Tex.). Further, using the protocol for the addition of labeled nucleotide in RNA transcription reactions as described in Ambion's MAXIscript kit, R6G labeled CTP nucleotide was incorporated into RNA (Rhodamine-6G-CTP, CAS #989-38-8, from NEN Life Sciences; Boston, Mass.).

Hybridization conditions were as follows. The buffer consisted of 6×SSPE (sodium chloride/sodium phosphate/ethylenediamine tetra-acetic acid (EDTA)), 0.005% TRITON X-100™ detergent, 0.1% w/v SDS (sodium dodecyl sulfate), 0.1% w/v BSA (bovine serum albumin, fraction V), 100 µg/ml hsDNA (heat-denatured herring sperm DNA). SSPE buffer components are described by Sambrook J. et al, in *Molecular Cloning: A Laboratory Manual* (Vol. 3, p. B 13; $2^{nd}$ Ed., 1989; Cold Spring Harbor Laboratory Press). The target, R6G-labeled G3PDH cRNA (SEQ ID NO: 1), was present at 1 nM.

The hybridization solution also included the positive control oligonucleotide, TAR25C, at 100 pM. TAR25C was used as the 5'-Cy3 (Cy3-TAR25C) (SEQ ID NO: 3). The positive control oligonucleotide hybridizes with the positive control probe, PRO25G (SEQ ID NO: 2), on the array surface. The labeled TAR25C oligonucleotides were prepared and HPLC-purified by Operon Technologies, Inc. (Alameda, Calif.). The PRO25G (SEQ ID NO: 2) and 5'-Cy3-TAR25C (SEQ ID NO: 3) sequences are:

SEQ ID NO: 2 5=-ATCATCGTAGCTGGTCAGTGTATCC-3=

SEQ ID NO: 3 5=-Cy3-GGATACACTGACCAGCTACGATGAT-3=

The target solution (400 µl) was allowed to hybridize with the array in a hybridization apparatus overnight (18 to 20 hours) at 37° C. with mixing on a rotary table.

Arrays were washed by first removing the hybridization target/buffer solution, flushing the hybridization chamber with 6×SSPE/0.005% TRITON X-100™ detergent, disassembling the hybridization chamber, and washing the array in a beaker of 0.1×SSPE/0.005% TRITON X-100™ at room temperature for 15 minutes with mixing.

The scanning equipment typically used for the evaluation of hybridized arrays includes a scanning fluorometer and is commercially available from different sources, such as Molecular Dynamics of Sunnyvale, Calif., General Scanning of Watertown, Mass., Hewlett Packard of Palo Alto, Calif. and Hitachi USA of South San Francisco, Calif. Analysis of the data, (i.e., collection, reconstruction of image, comparison and interpretation of data) is performed with associated computer systems and commercially available software, such as IMAGEQUANT™ by Molecular Dynamics (Sunnyvale, Calif.) or GENECHIP™ by Affymetrix (Santa Clara, Calif.).

The light source, typically from a laser, generates a collimated beam. The collimated beam sequentially illuminates small surface regions of known location. The resulting fluorescence photons from the surface regions are collected either confocally or non-confocally. The collected photons are transmitted through appropriate spectral filters, to an optical detector. A recording device, such as a computer memory, records electronic signals from the detector and builds up a raster scan file of intensities as a function of position, or time as it relates to the position. Such intensities, as a function of position, are referred to as "pixels". The pixels within a region centered upon the expected or intended position of a feature can be averaged to yield the relative quantity of target hybridized to the probe in that feature, if the expected or intended position of the feature is sufficiently close to its true position. For a discussion of the optical scanning equipment, see e.g., U.S. Pat. No. 5,760,951 (confocal scanner) and U.S. Pat. No. 5,585,639 (off axis scanner); the disclosures of which are herein incorporated by reference.

FIG. 1 illustrates the results of a hybridization assay, wherein arrays containing probes designed to hybridize with G3PDH cRNA were hybridized to R6G-labeled G3PDH cRNA (SEQ ID NO: 1). The features that yielded minimal signal (labeled as Background Features in FIGS. 1 and 2) were tested on multiple arrays for their ability to hybridize to their specific labeled G3PDH cRNA target and in all cases were found to yield minimal signal. These empirically observed background probes are shown in Table 1. Additionally, probes that were designed to hybridize to cRNA of a portion of the P53 gene (human tumor suppressor p53 gene; target polynucleotide (SEQ ID NO: 4) is the Watson-Crick complement of the mRNA) and those found to yield minimal signal with R6G-labeled P53 cRNA (SEQ ID NO:4) are also shown in Table 1.

ment was performed that contained five heterologous targets ("xenogenes") in a labeled human liver cRNA pool. The xenogenes used were cab, cor47, sig1, pbp1 and pbp2 (see Table 2 for gene information; target polynucleotides are the Watson-Crick complements of the mRNA). The array contained features of the positive control probes (SEQ ID NOs: 2 & 3), background probes (SEQ ID NO: 17), and probes that were being tested for their specific hybridization to the xenogene targets.

TABLE 1

| Probe Number | Source Gene | Sequence ID Number | Sequence, 5' to 3' |
| --- | --- | --- | --- |
| 41 | Human p53 | SEQ ID NO: 5 | CAGAGGAAGAGAATCTCCGCAAGAA |
| 51 | Human p53 | SEQ ID NO: 6 | GAATCTCCGCAAGAAAGGGGAGCCT |
| 81 | Human p53 | SEQ ID NO: 7 | CGAGCTGCCCCCAGGGAGCACTAAG |
| 91 | Human p53 | SEQ ID NO: 8 | CCAGGGAGCACTAAGCGAGCACTGC |
| 221 | Human p53 | SEQ ID NO: 9 | TGAATGAGGCCTTGGAACTCAAGGA |
| 241 | Human p53 | SEQ ID NO: 10 | AAGGATGCCCAGGCTGGGAAGGAGC |
| 251 | Human p53 | SEQ ID NO: 11 | AGGCTGGGAAGGAGCCAGGGGGGAG |
| 261 | Human p53 | SEQ ID NO: 12 | GGAGCCAGGGGGAGCAGGGCTCAC |
| 150 | Human G3PDH | SEQ ID NO: 13 | TGGGCTACACTGAGCACCAGGTGGT |
| 210 | Human G3PDH | SEQ ID NO: 14 | AATATGATGACATCAAGAAGGTGGT |
| 310 | Human G3PDH | SEQ ID NO: 15 | ATCCCTGAGCTAGACGGGAAGCTCA |
| 390 | Human G3PDH | SEQ ID NO: 16 | AACTGTGGCGTGATGGCCGCGGGGC |
| 570 | Human G3PDH | SEQ ID NO: 17 | GTGTGAACCATGAGAAGTATGACAA |
| 580 | Human G3PDH | SEQ ID NO: 18 | TTCGTCATGGGTGTGAACCATGAGA |

Figure 2:
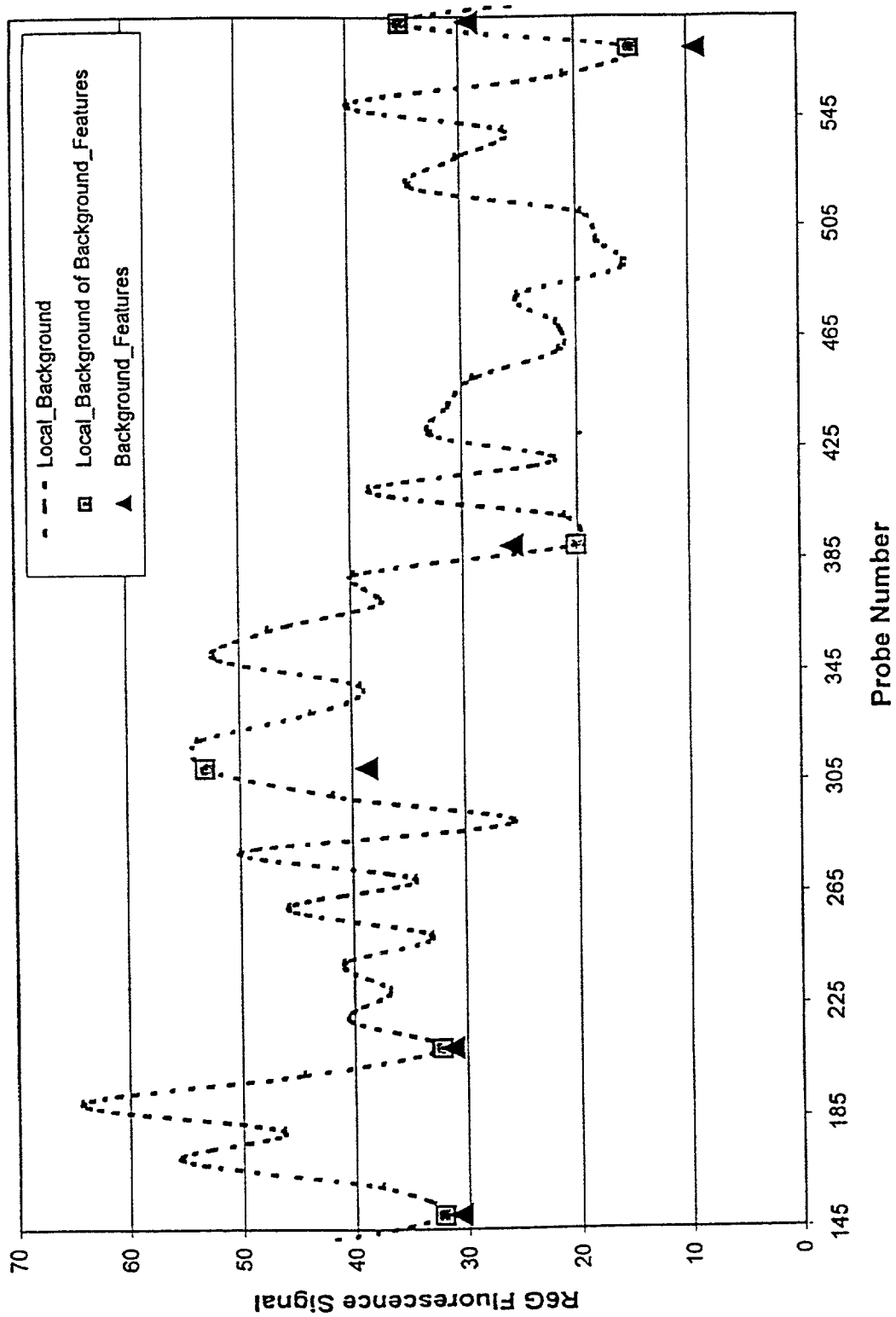
FIG. 2 is a magnified view of a portion of FIG. 1, showing the signal of features containing the empirically observed background probes, and the signal from the local background outside the features.

FIG. 2 represents a magnified view of the background feature signal from FIG. 1. In addition, the local background signals from this region of the array are shown, with symbols highlighting the signal from the local background surrounding each of the background features. As illustrated in FIG. 2, the signal of the background features is often less than the signal of the surrounding local background. As discussed above, it is common practice to subtract the local background surrounding a given feature from the signal of that feature, in order to obtain background-corrected signal values. If this were done with the background features seen in FIG. 2, the background-corrected signal would be negative for five of the six features. It is also clear from FIG. 2 that the signal from the background features follows the same general trend as the signal from the local background (i.e. they are sensitive to local variations in the background signal).

EXAMPLE 2

Utilization of Empirically Observed Inactive Probes

The empirically observed background features were tested against other purified cRNA labeled targets as well as a labeled complex cRNA pool from human liver. An experi-

TABLE 2

| Gene | Source | Sequence ID Number | GenBank Accession Number | Function |
| --- | --- | --- | --- | --- |
| cab | *Arabidopsis thaliana* | SEQ ID NO: 19 | X56062 | chlorophyll binding |
| cor47 | *Ar. thaliana* | SEQ ID NO: 20 | X59814 | ABA-mediated cold response |
| sig1 | *Ar. thaliana* | SEQ ID NO: 21 | AF015542 | chloroplast sigma factor |
| pbpC1 (5'-clone) herein referred to as pbp1 | *Escherichia coli* | SEQ ID NO: 22 | U88571 | peptidoglycan cross-linking |
| pbpC1 (3'-clone) herein referred to as pbp2 | *E. coli* | SEQ ID NO: 23 | U88571 | peptidoglycan cross-linking |

The R6G-labeled cRNA xenogene targets were all present at 30 pM. The R6G-labeled human liver cRNA was present at 150 μg/ml. It was found that the presence of the complex pool cRNA greatly increases the signal of the local background, compared with arrays without complex pool RNA, making the background features even more visible as "negative features."

The background features were thus validated to yield minimal signal when presented with the five labeled xenogene targets and the labeled complex human liver cRNA pool. Other experiments further validated that labeled complex cRNA pools from yeast and mouse also yielded minimal signal with the background features.

The appearance of "negative features" is not a requirement for background probes, although "negative features" were consistently observed during the initial experiments discussed above. Other types of array surfaces or variations in the methods used to hybridize or wash the arrays can change the nature of the background signal of the local background such that "negative features" are no longer visible.

EXAMPLE 3

Probes Forming Highly Stable Intramolecular Structures

Probes were designed to form highly stable intramolecular secondary structures. Such structures are well known to the art and include hairpins and pseudo-half knots. It was hypothesized that such probes would hybridize poorly to any target and would possess nonspecific binding properties similar to those of hybridization probes; thus, these probes would be good candidates for background probes.

A. Design of Hairpin Probes as Background Probes

The design of these probes utilized stable base pairing for the stem portion and utilized variations of the "GAAA" sequence with a C:G clamp for the tetra-loop portion of the structure (Antao, V. P. et al., *Nucleic Acids Research*, 1991, 19:5901–5905). Multiple structures were designed and the self-structure properties of the probes were calculated using published thermodynamic parameters and known algorithms, such as the "MFOLD" method (Jaeger, J. A. et al., *Proc. Natl. Acad. Sci.*, 1989, 86:7706–7710; and Li, Y. and W. D. Wilson, *Biochemistry*, 30:7566–7572). Representative probes are listed in table 3 and were studied further.

TABLE 3

Designed hairpin probes

| Probe Name | Sequence ID Number | Sequence | Predicted $T_m$ (° C.)* |
|---|---|---|---|
| ST1 | SEQ ID NO: 24 | GCTAGCGAAAGCTAGC | 83 |
| ST2 | SEQ ID NO: 25 | GCGAGCGAAAGCGAGC | 71 |
| ST3 | SEQ ID NO: 26 | GCAGGCGAAAGCAGGC | 48 |
| ST4 | SEQ ID NO: 27 | GCAGGGGAAAGCAGGC | <30 |
| ST5 | SEQ ID NO: 28 | GCATACCGAAGCACGC | <44 |

*Melting temperature were predicted according to the methods described by Jaeger, et al. and Li, et al.

The self-structure properties of the probes was experimentally verified to form highly stable intramolecular duplex structures by measuring the DNA $T_m$ as a function of oligonucleotide concentration. DNA $T_m$'s were measured using a commercially available apparatus, the Perkin-Elmer UV/VIS Spectrometer model Lambda 14. Solutions of test oligonucleotides, ranging from 0.2 to 10 optical densities (measured at 260 nm), were made with 6xSSPE buffer (described above in Example 1). The absorbance at 260 nm was followed from 20° C. to 95° C., ramping at 0.5° C./minute. Data analysis was performed using the spectrometer's "Pick Peak" function.

A high, concentration-independent, duplex melting temperature demonstrates the formation of a stable intramolecular secondary structure. For example, a 16-mer DNA oligonucleotide, ST1 (SEQ ID NO: 24), exhibited a concentration-independent solution melting temperature of about 80° C., presumably due to formation of the intramolecular secondary structure illustrated below:

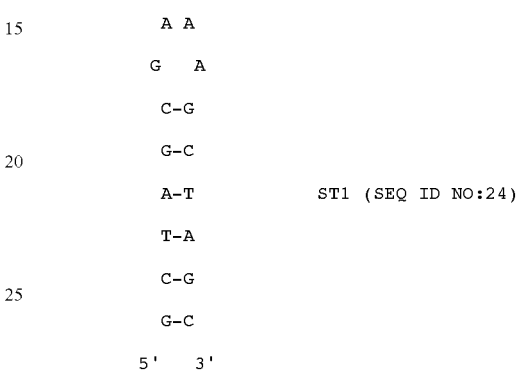

B. Testing of Designed Hairpin Probes as Background Probes

The designed probes from Table 3 were tested as background probes by designing an array that contained features from these probes, along with features of the validated G3PDH-570 background probe (SEQ ID NO: 17). R6G-labeled yeast cRNA pool target was hybridized to this array. Probe synthesis on the array, and conditions used for hybridization, washing, and scanning were as described Example 1 above, with the exception that the hybridization buffer contained no BSA or SDS.

Figure 3:
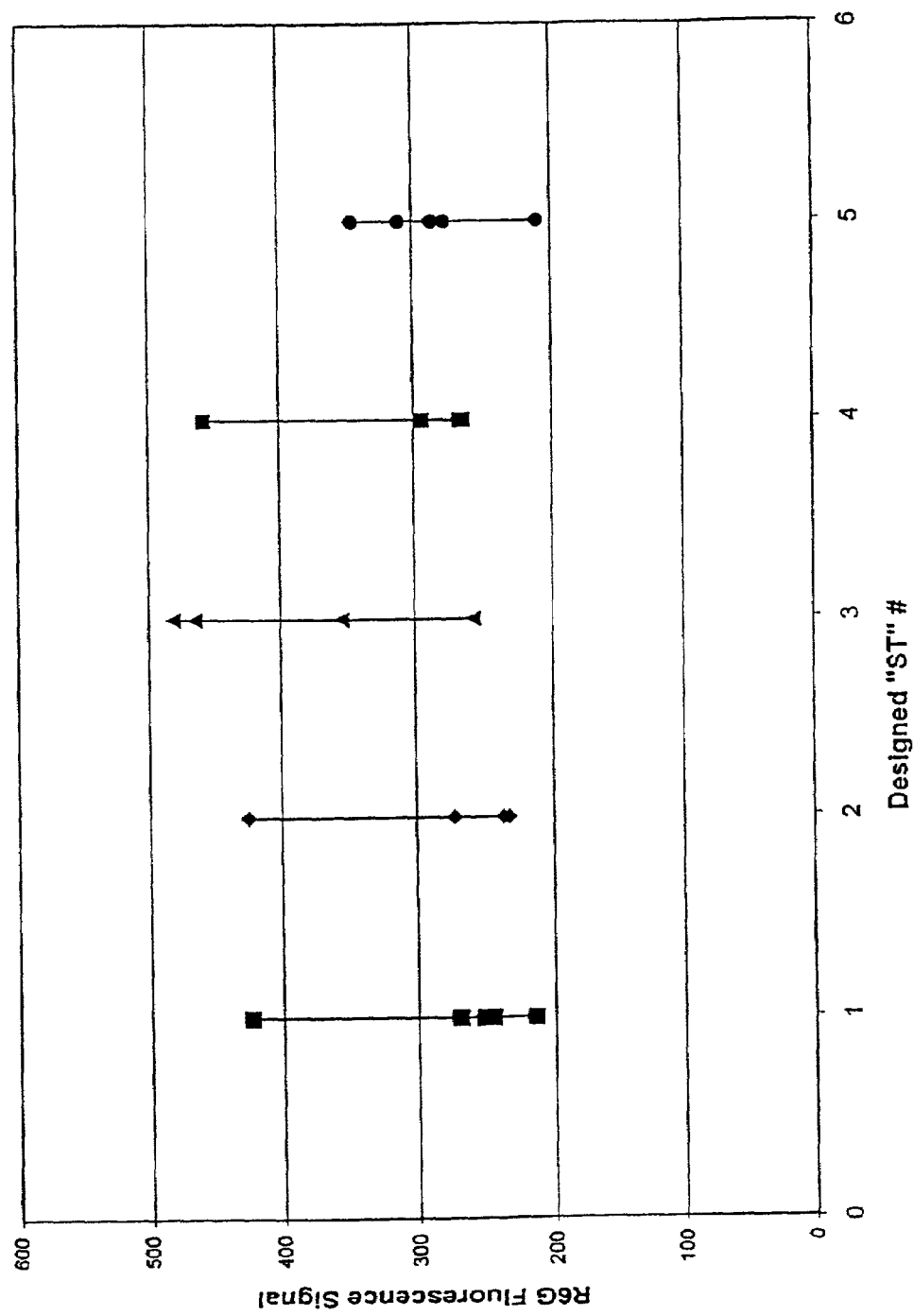
FIG. 3 illustrates the results of a hybridization assay, wherein the designed hairpin probes were hybridized to R6G-labeled yeast cRNA.

FIG. 3 illustrates the results of testing designed hairpin probes as background probes, and demonstrates that all of the hairpin probes listed in Table 3 (i.e. SEQ ID NO: 24–28) yielded minimal signal, indicating poor hybridization to the labeled yeast RNA pool target. The signal of the hairpin probe features was similar to the signal of the validated G3PDH-570 background probe features (average signal=258 counts, SD=32, 13% CV; SEQ ID NO: 17). The background features (i.e. SEQ ID NO: 17 and 24–28) were observed as "negative features" in the scanned image. Table 4 summarizes the average, inter-feature standard deviation and inter-feature % CV for the five designed hairpin probe features (25 replicates in total) compared with the statistics of the local backgrounds surrounding these features.

TABLE 4

Signal statistics of hairpin probe features and of local background

|  | Features | Local Background |
|---|---|---|
| Average | 319 | 934 |
| SD | 94 | 382 |
| % CV | 30% | 41% |

Table 4 shows the variation of the signal between replicate features of the hairpin probe features (e.g. absolute inter-feature SD's and relative inter-feature % CV) was lower than variation of signal between the local backgrounds surrounding these features. Thus, the hairpin probe features not only yielded lower signal than the surrounding local backgrounds, but the signal from the hairpin probe features was also more consistent, regardless of the location on the array.

EXAMPLE 4

Short Probes

The melting temperature of shorter duplexes is dependent upon length, unlike the DNA duplexes longer than about 100 base pairs, wherein the melting temperature is dependent upon strand concentrations and fraction (G+C). The average predicted melting temperature for a set of 10,000 random DNA 25-mers with an average fraction (G+C) of 0.5 is 69° C., while the average predicted melting temperature for a corresponding set of DNA 15-mers is 46.9° C. (assuming 100 pM target strand and 1M salt). The decrease in melting temperature is related to increase in the relative entropic cost of duplex formation as the strands grow shorter. Thus, it was hypothesized that using shorter probes as background probes would result in minimal binding of target.

Variable lengths of probes were designed in order to determine the shortest length that is still effective background probes. Empirically, the correct length of probe should be found such that the nonspecific binding properties of surfaces bearing these short probes mimics the properties of surfaces bearing long probes (e.g. 25-mers). Such regions would possess similar surface energy properties as regions bearing longer probes, but would exhibit reduced affinities for their complementary target sequences, when employed under conditions that are optimal for longer probes.

The effect of probe length on background signal was determined in the same array used to assess the background signal properties of the hairpin probes (i.e. Example 3). Probes of length 5, 10, 15, and 20 nucleotides were designed by progressively shortening the empirically observed inactive probe G3PDH-570 (SEQ ID NO: 17) from its 5'-end (i.e. the end opposite from the site of attachment to the array surface). These shortened probes are shown in Table 5.

TABLE 5

Sequences of Shortened probes and original probe sequence

| Probe Length | Sequence ID Number | Sequence |
| --- | --- | --- |
| 25 | SEQ ID NO: 17 | GTGTGAACCATGAGAAGTATGACAA |
| 20 | SEQ ID NO: 29 | AACCATGAGAAGTATGACAA |
| 15 | SEQ ID NO: 30 | TGAGAAGTATGACAA |
| 10 | SEQ ID NO: 31 | AGTATGACAA |
| 5 | SEQ ID NO: 32 | GACAA |

Figure 4:
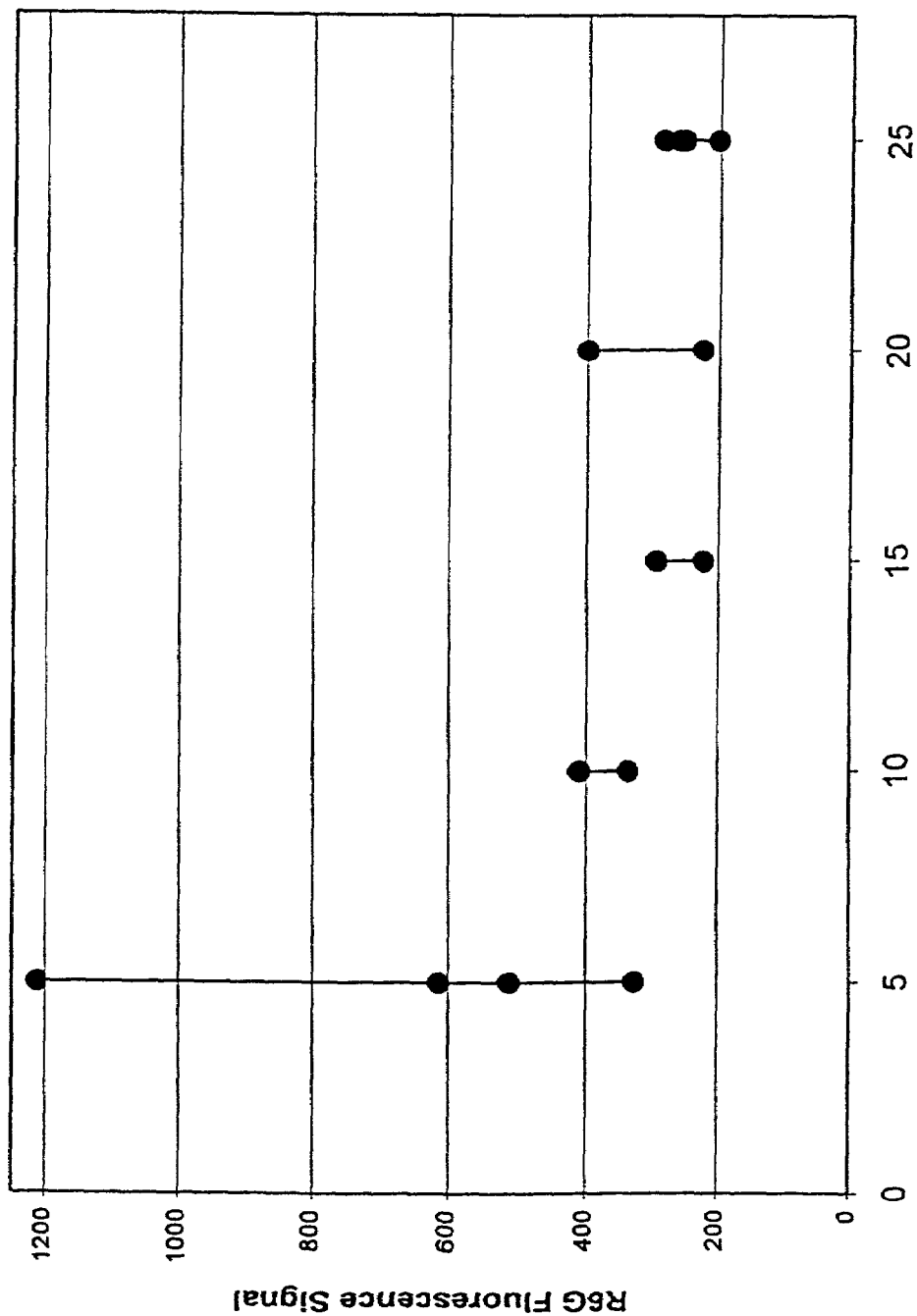
FIG. 4 illustrates the results of a hybridization assay, wherein the shortened G3PDH-570 probes (SEQ ID NO:17, 29–32) were hybridized to R6G-labeled yeast cRNA.

FIG. 4 illustrates the results of a hybridization assay, wherein the shortened G3PDH-570 probes were hybridized to R6G-labeled yeast cRNA. The background features (I.E. SEQ ID NO: 17 and 29–32) were observed as "negative features" in the scanned image. The 20-, 15-, and 10-mer probes (SEQ ID NO: 29–31) consistently yielded minimal signal. Table 6 summarizes the average, inter-feature standard deviation and inter-feature % CV for the two best shortened probes (SEQ ID NO: 29 and 30), the parent 25-mer G3PDH-570 probe features (SEQ ID NO: 17), and the local backgrounds surrounding these features.

TABLE 6

Signal statistics of variable-length probe features and of local background

| | Seq ID | | |
| --- | --- | --- | --- |
| | #17 | #29 & 30 | |
| | Probe Length | | |
| | 25-mer | 20 & 15-mer | Local Background |
| Average | 258 | 297 | 694 |
| SD | 32 | 92 | 328 |
| % CV | 13% | 31% | 47% |

As discussed in Example 3, the background probe features provide a lower and more consistent estimate of background signal than do the local background measurements.

EXAMPLE 5

Chemically Modified Probes

A background probe can also be produced by the synthesis of oligomeric abasic phosphodiesters containing a substituted ribose, or ones where the substituted ribose has been replaced by another moiety such as a polyether. Such abasic phosphodiesters possess polyelectrolyte properties similar to normal DNA and yield a surface with similar nonspecific binding properties as surfaces bearing normal DNA strands, but are unable to hydrogen bond to target species containing nitrogenous bases.

Examples of several phosphoramidite monomers useful to construct an abasic phosphodiester oligomer, using standard chemical synthetic techniques, are shown in FIG. 5. In structure I, the nitrogenous base in the deoxyribose sugar ring is replaced with hydrogen. In structure II, the deoxyribose sugar ring is replaced by a triethylene glycol unit. Analogs of Structure II are obtained by replacing triethylene glycol with monoethyleneglycol and hexaethyleneglycol. Compounds of Structures I and II are commercially available (Glen Research, Sterling, Va.).

Further examples of modified DNA probes include probes comprising reverse polarity nucleotide analogs, i.e. probes wherein the deoxyribose sugar-nitrogenous base backbone comprises certain nucleotides attached such that they are in opposite polarity as compared to the adjacent nucleotides. (See U.S. Pat. Nos. 5,399,676; 5,527,899 and 5,721,218 and Koga, M. et al. (1991) J. Org. Chem. 56:3757–3759), the disclosures of which are herein incorporated by reference.

The methods described in Example 1 above enable the synthesis of background probes made with modified nucleotides. The use of such background probes in hybridization arrays permits an accurate estimation of the background signal of hybridized array features. Additionally, such estimation of the background allows for a lower limit of detection (LLD) for the desired target molecule.

EXAMPLE 6

Use of Background Features in Background-correcting the Signal of Hybridization Features The array of Example 2 was hybridized with the R6G-labeled xenogene cRNA's present at 30 pM and was part of a series of arrays that were hybridized with variable concentrations of the xenogene targets. The purpose of the series of arrays was to determine the LLD of specific probes against the five xenogene targets. This series of experiments is referred to as the xenogene titration experiment. In order to determine LLD's, one must first background-correct the total signal observed in each feature. The effect of using background features vs. local background for background-correction is demonstrated in this example. The example uses the hybridization data of the R6G-labeled cor47 and pbp2 cRNA targets with their respective specific probes, cor47-181 (SEQ ID NO: 33) and pbp2-867 (SEQ ID NO: 34):

SEQ ID NO: 33    AGGAGAACAAGATTACTCTGCTAGA

SEQ ID NO: 34    TTCGTTTCCCCATCTGGCTGGATGA

The probes cor47-181 (SEQ ID NO: 33) and pbp2-867 (SEQ ID NO: 34) were each present in four replicate features on the array. There were 17 replicates of background features (N=9 replicates of G3PDH-570; SEQ ID NO 17 and N=8 replicates of ST1; SEQ ID NO: 24). The array had 200 features total and the regions around each of these features comprised the 200 regions of local background. Table 7 shows the statistics of the background features and local backgrounds.

TABLE 7

Signal statistics of background features and of local background

|  | Background Features | Local Background of All Features |
|---|---|---|
| N | 17 | 200 |
| Minimum | 13 | 35 |
| Average | 20 | 108 |
| SD | 8 | 123 |
| % CV | 41% | 114% |
| 3 *SD | 24 | 369 |

The average signal from the background features is much lower than the average of the local background (i.e. 20 <108). Replicate features are shown for the PRO25G positive control oligonucleotide (SEQ ID NO: 2), the background probe ST1 (SEQ ID NO: 24), as well as two replicates of the pbp2-867 probe (SEQ ID NO: 34). The signals from the pbp2-867 (SEQ ID NO:34) features (i.e. features #112 and #118) are of similar strength as some portions of the local background signal, but they are stronger than the signal from the background features.

The quantitative signal data for the array region around pbp2-867 feature #118 (SEQ ID NO: 34) is shown in FIG. 6 (area of magnification indicated in FIG. 3). The positive control features (SEQ ID NO: 2; average signal=4,280) have been omitted from this figure in order to magnify the signal scale for the features of interest. FIG. 6 shows that the signals from the local backgrounds are greater than the two background features, #115 (ST1; SEQ ID NO: 24) and #131 (G3PDH-570; SEQ ID NO: 17). The signal from feature #118 (pbp2-867 probe; SEQ ID NO: 34) is greater than the local background, but it is even greater than the background features. Thus, the background-corrected signal for feature #118 (SEQ ID NO: 34) is greater when corrected with background features (net signal=123; Table 8) than when corrected with local background (net signal=69; Table 8).

TABLE 8

Signal statistics of pbp2-867 replicate features

| | | | | Corrected with: | |
|---|---|---|---|---|---|
| Feature # | Uncorrected Signal | Local Background Signal | Local Background | Global Background (min = 35) | Background Features (average = 20) |
| 16 | 208 | 48 | 159 | 173 | 188 |
| 61 | 239 | 80 | 159 | 205 | 220 |
| 112 | 159 | 73 | 86 | 124 | 140 |
| 118 | 142 | 74 | 69 | 108 | 123 |
| Inter-feature Average | 187 | — | 118 | 152 | 167 |
| Inter-feature SD | 44 | — | 48 | 44 | 44 |

Another common method of background-correction is to use the minimum of all local backgrounds, referred to in these examples as the global background (signal=35; Table 7). The use of this global background to background-correct feature #118 (SEQ ID NO: 34) yields a signal of 108 (Table 8). Table 8 also shows the different background-corrected values that are obtained for the other three replicate features of probe pbp2-867 (SEQ ID NO: 34). With all four of the pbp2-867 (SEQ ID NO: 34) features, the use of background features yields the highest background-corrected signals.

The above analysis was performed on all 158 hybridization features of this array. The results were the same as observed with the four features of the pbp2-867 (SEQ ID NO: 34) probe. Thus, the use of background features, as opposed to local background or global background, yielded the highest signal values of all background-corrected feature signals. However, in order to establish background features as the best background-correction method, the background-corrected signals need to be accurate, as well as yield higher signal values.

One measure of the accuracy of a background correction method is the degree with which the method compensates for variations in the background signal. The use of local backgrounds for background correction of features assumes that the different signal values detected at the different local background regions reflects the actual background signal in their respective neighboring features. This hypothesis was tested by comparing the reproducibility of signals among replicate features of the same hybridization probe. If the above assumption of local background correction is correct, the reproducibility of signals among replicate features should be better when corrected with the local background method than when uncorrected or when background-corrected with a constant value of background. However, this was not the case in the probes studied.

Figure 7:
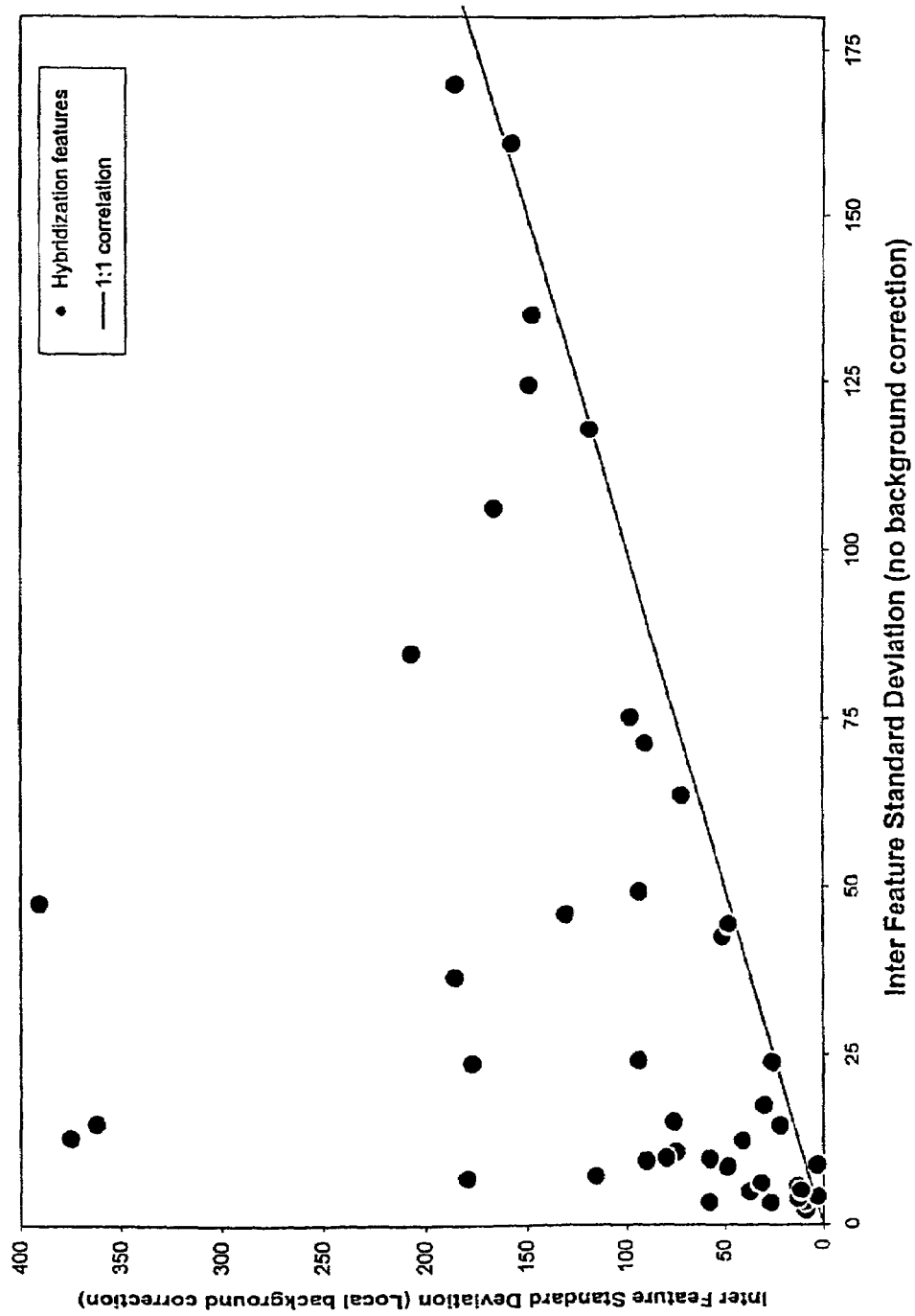
FIG. 7 demonstrates the inter-feature standard deviations (interfeature_SD) of signal from replicate features of hybridization probes, wherein the standard deviations are calculated with or without local background correction. The five arrays contained specific features to five xenogenes, positive control features, and background features. The arrays were hybridized to R6G-labeled cRNA from five xenogenes, ranging from 3 pM to 3000 pM, as well as R6G-labeled human cRNA pool target.

For instance, with the four replicates of the pbp2-867 probes (SEQ ID NO: 34), the inter-feature variation (calculated as the standard deviation (SD) among the four feature signal values) was 48 when corrected with local background, as opposed to 44 with no background-correction or with a constant value of background-correction (see Table 8). This same analysis was performed with the inter-feature standard deviations of the four replicates from each of the 42 xenogene hybridization probes. FIG. 7 shows that the inter-feature standard deviations (inter-feature SD) were increased when the feature signals were corrected with the local background method, as opposed to no background-correction (i.e. SD values above the 1:1 correlation line). The increase in inter-feature SD was 62 signal counts on average, and as high as 362 signal counts. There were three exceptions to this observation. In the three cases where the use of local background correction decreased the inter-feature SD, the signal values decreased by less than 6 counts.

These results illustrate that background-correction using local background generally made the inter-feature statistics worse, indicating that the background signal reported in a given local background region did not track the actual background signal within its neighboring feature. Background correction with a constant value yielded more accurate feature signals.

The same conclusion was arrived at by studying the average inter-feature % CV metric ([inter-feature standard deviation of replicates/inter-feature mean of replicates]× 100%). This metric used signals before background correction in order to determine the magnitude of variability among replicate feature signals, and to determine which background method most closely modeled that variation. The inter-feature % CV of the four replicates from each of the 42 xenogene hybridization probes was calculated and yielded an average of 25% CV and a maximum of 47% CV. This variation among replicate features is more closely modeled by the inter-feature variation of the background features than by the variation of local backgrounds (i.e. 41% CV and 114% CV, respectively; Table 7). Thus, the local background method samples a more variable source of background signal, as well as a higher level of background signal, than the background feature method.

Studies comparing the two constant type background-correction methods (i.e. global background and background features) are described below. In order to determine the accuracy of global background vs. background features, features with low signal values from five of the arrays of the xenotitration experiment (i.e. those with target concentrations ranging from 3 pM to 3,000 pM) were studied.

Figure 8:
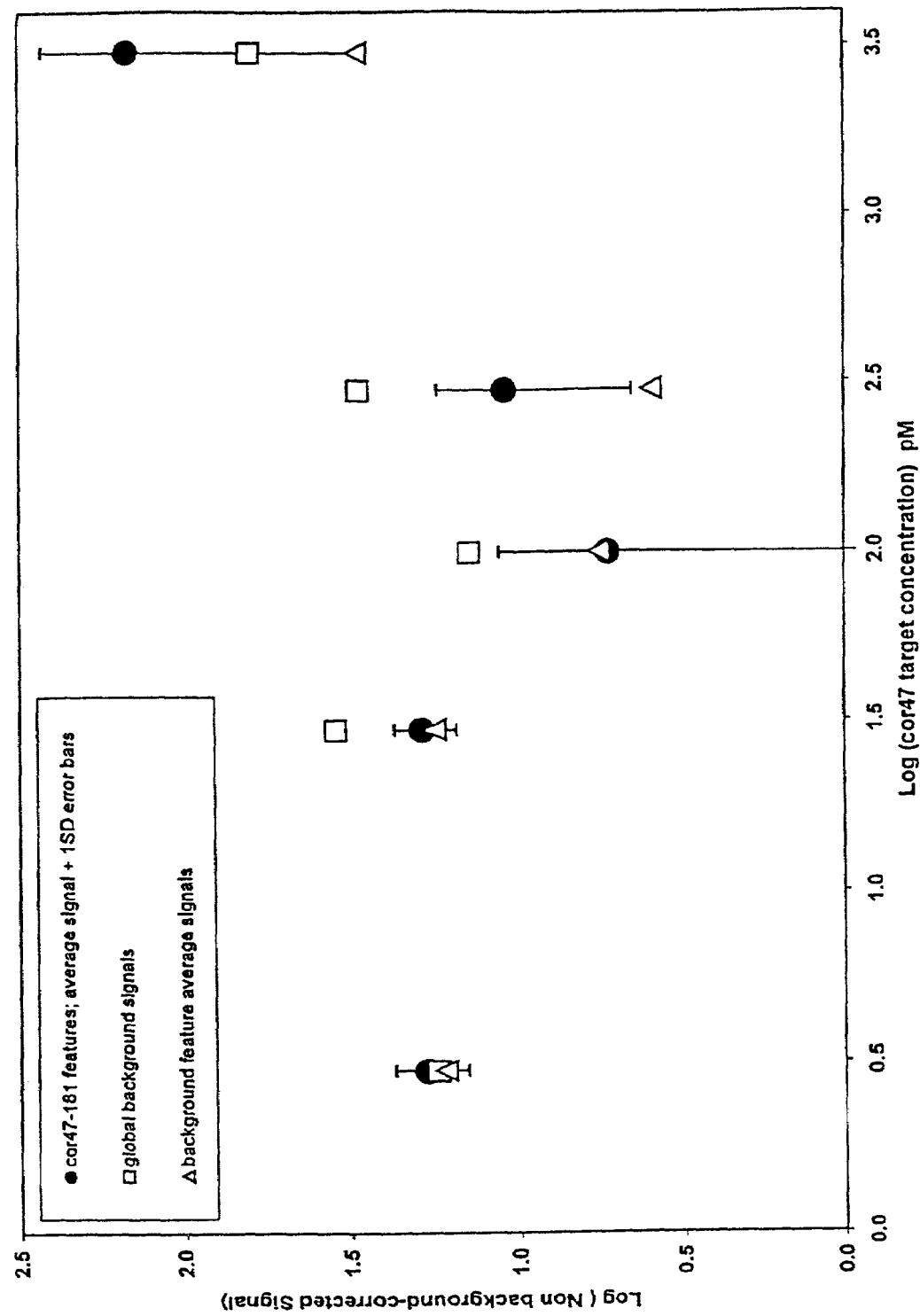
FIG. 8 illustrates signal statistics of one probe, cor47-181 (SEQ ID NO:33) across the five arrays described in FIG. 7. The global background and average background feature signals from each array are also shown. The background features accurately model the cor47-181 (SEQ ID NO: 33) features that have low signals, while the global background overestimates these background signals.

Low signal values were obtained with some probes that poorly hybridized with their correct target at all but the highest target concentration. Other probes yielded low signals only at the lowest target concentrations. An example of a poorly hybridizing probe, cor47-181 (SEQ ID NO: 33), is shown in FIG. 8. The mean of the uncorrected replicate cor47-181 (SEQ ID NO: 33) feature signals and 1×SD error bars (i.e., inter-feature standard deviation) are illustrated for five target concentrations. The average background feature signal and global background signal from each of the arrays is also plotted. At a target concentration of 300 pM (log concentration=2.5), the signals from the replicate features of probe cor47-181 (SEQ ID NO: 33) were greater than the signal of the background features, but less than the signal of the global background. At the target concentrations of 30 pM and 100 pM (log concentration=1.5 and 2.0), the signals of the cor47-181 (SEQ ID NO: 33) probes were within the distribution of the background features and, again, lower that the global background signal. At the target concentrations of 3 pM (i.e. log concentration=1.5) and 0 pM (not shown on the log plot), the signals of the cor47-181 (SEQ ID NO: 33) probes were within the distribution of the background features and within 4 signal counts of the global background signal.

FIG. 8 demonstrates that the average signal from the background features closely models the low signals observed from the cor47-181 (SEQ ID NO: 33) features. In contrast, the global background overestimates the background signal for three arrays (at 30, 100 and 300 pM target concentrations) and correction with the global background yields negative net signals for these probes. The local background signals surrounding each of the cor47-181 (SEQ ID NO: 33) probe features are not shown in FIG. 8, but these signals are even greater than the global background signal, since the global background signal used from each array is the minimum of all local background signals from that array.

A similar analysis was performed with the inter-feature means of all 42 xenotitration hybridization probes from the 5 arrays (target concentrations from 3 pM to 3,000 pM). Of the 210 total inter-feature means, 190 inter-feature means were greater than either the global background or the background feature significant limit of their respective arrays. The signal value used for the background feature significant limit of each array is the sum of the background features mean and [1×Background_SD (b-SD)], where the Background_SD (b-SD) is defined as the inter-feature standard deviation among the background features of that array. This metric is used to determine the significance of feature signal values to be used in LLD calculations, as discussed below in Example 7. The signal characteristics of the lowest 20 inter-feature means are shown in Table 9:

TABLE 9

Xenotitration hybridization probes
Distribution of lowest signal inter-feature means

| Inter-feature means | N | Characterized as |
| --- | --- | --- |
| > Background Feature (Mean + 1x SD) & < Global Background | 13 | Significant using background features, not significant using global background |
| Within Background Feature (Mean +/− 1x SD) & < Global Background | 4 | Similar distribution as background |
| Within Background Feature (Mean +/− 1x SD) & <= Global Background | 3 | Similar distribution as background features and global background |

The use of background features for background-correction yields thirteen probes with significant signal and four probes which were of the same distribution as the background features. Global background overestimated the background signal for these seventeen probes. Additional evidence for the accuracy of the background features vs. global background (in context of LLD calculations) is described in Example 7, infra.

EXAMPLE 7

Use of Background Features in Determinations of LLD

This example demonstrates the impact that different background-correction methods have on the calculation of Lower Limit of Detection (LLD). As demonstrated in Example 6, the background signal values using background features are generally lower than the signals using either the local or global background methods. Additionally, the variation of signal among background feature replicates is much less than the variation among local background regions (see, e.g., Tables 4, 6 and 7).

The variation of background signal (i.e. the noise of the background signal) is important since it is used in calculations to determine whether a feature is "significant". A standard deviation (1×b-SD) of the background, used as the noise, must be exceeded for a background-corrected feature to be significant. For the background feature method and the global background method, the noise metric is the inter-feature standard deviation (e.g. signal=8 vs. 123, respectively; Table 7). Since the local background method uses only one signal value per local background region to background-correct its respective neighboring feature, there is no inter-feature standard deviation. The noise metric for local background is defined as the intra-feature standard deviation (pixel signal variation) of the local background region.

Figure 9:
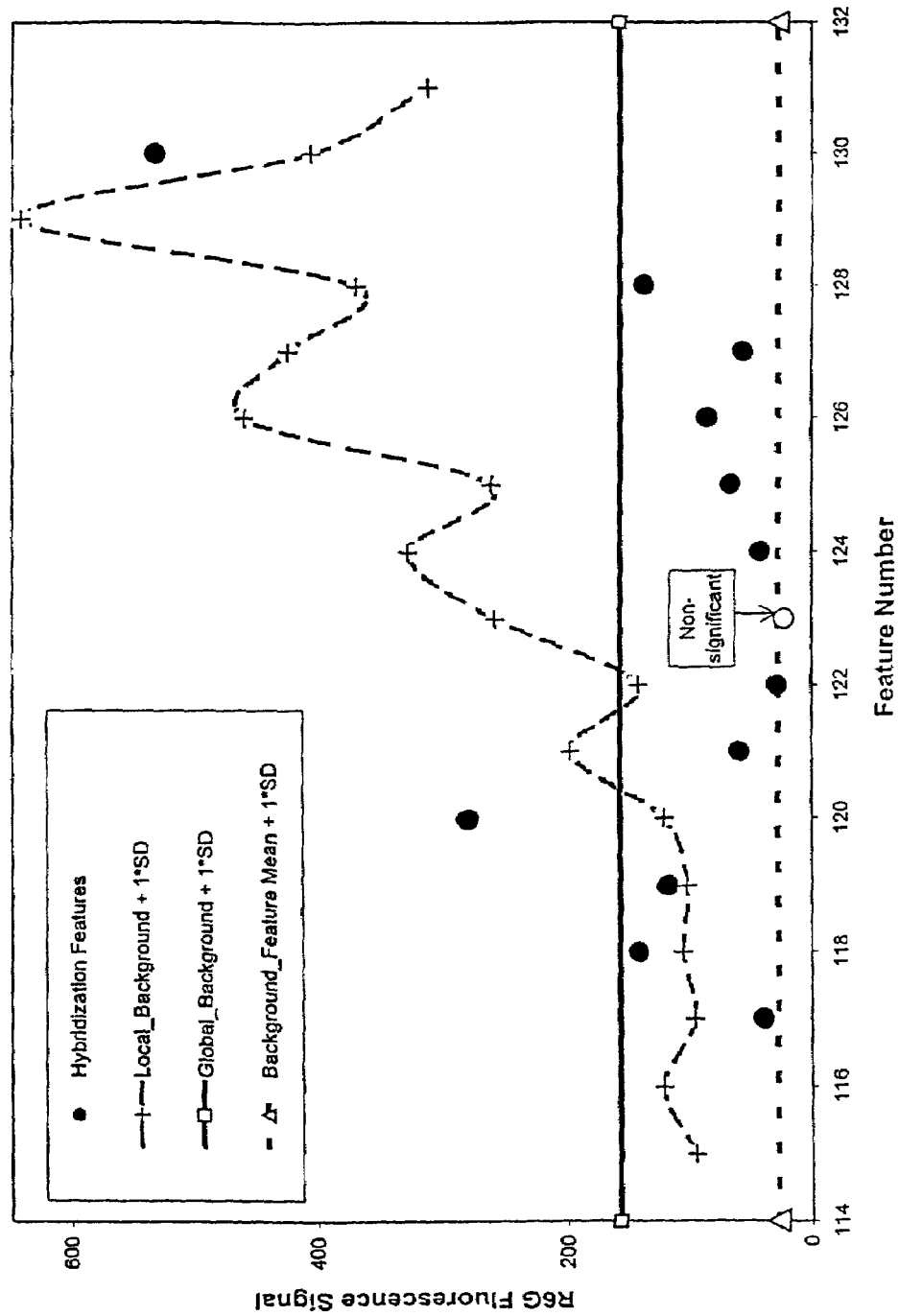
FIG. 9 uses the non-background-corrected signal data from FIG. 6 and compares the threshold limits of signal significance using three methods: background features, local background, and minimum global background. The figure illustrates the effect of background overestimation on data analysis: hybridization features that are significantly different from the threshold using background features are not significant when using either local or global background thresholds.

As discussed above, features with low observed signals may or may not exceed significant limits, depending upon the background-correction method used (e.g. Table 9). A graphical representation of the analysis is illustrated in FIG. 9, using the same array and feature region used for FIG. 6. In order to compare the differences among the three background methods on the same figure, the background-uncorrected signals of hybridization features are used. The background-uncorrected signal is significant if it is greater than the sum of the estimated background signal and (1×b-SD) for each of the three background-correction methods. In addition to illustrating the signal from hybridization features, the significance limits for each of the three background-correction methods are also demonstrated in FIG. 9. With the background feature method, 12 of the 13 hybridization features were significant. In contrast, only 2 or 4 hybridization features were significant with the global background method or local background method, respectively. The analyses of FIG. 9 and Table 9 demonstrate that the use of background features, as compared to local background or global background, permits more features to be identified as significant, and thus to be used in LLD calculations.

The following section describes the algorithm used for LLD calculations. All hybridization features which pass the background significance test, described above, are averaged for a given probe for each array. A plot of log(background-corrected signal) vs. log(target concentration) is plotted for each probe. If a probe has not passed the significance test at a given target concentration, the background significance signal value (1×b-SD) is used for the "y" value at that array concentration. A linear regression calculation is performed on the linear portion of the data. The LLD concentration is calculated at the point where the best fit linear regression line crosses a threshold. The threshold for these LLD calculations is calculated as (3×average b-SD). The b-SD values are calculated for each array, as described above. The average of the five array values is multiplied by three for the LLD threshold (3×average b-SD). An example of an LLD calculation is shown in FIG. 12 for the probe, pbp1-203 (SEQ ID NO: 35):

SEQ ID NO: 35    GGTTATTTCCGGTGGCAGCACGCTC

Figure 12:
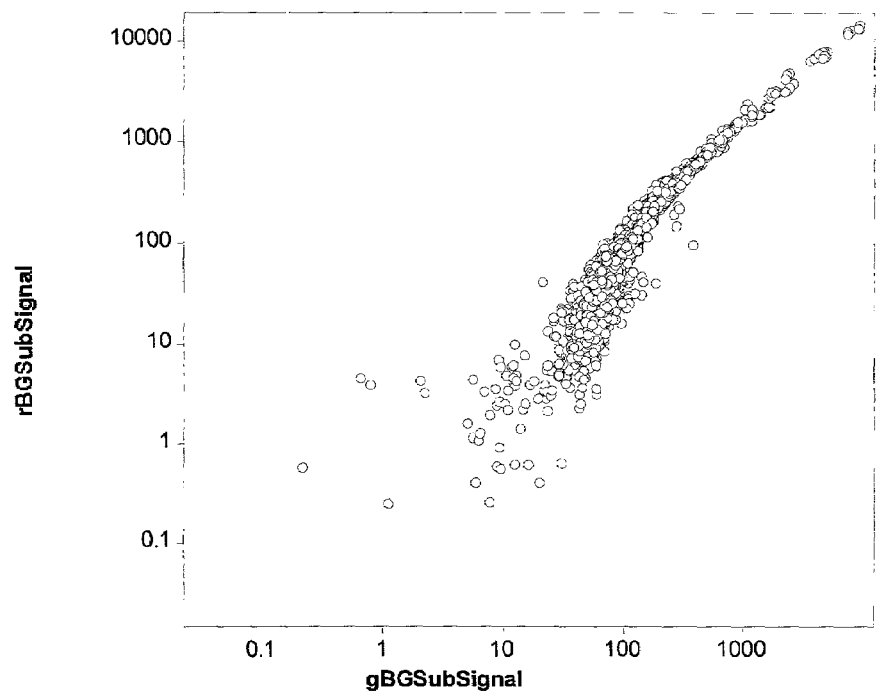
FIG. 12 provides a graphical representation of the results obtained from a two-color self-self hybridization assay using the background feature ProST1.

FIG. 12 compares the background feature method with the global background method. The comparison does not include the local background method, since the data presented in Example 6, especially FIG. 9, demonstrated the deficiencies of this method. For purposes of demonstrating both background-correction methods on the same figure, the non-background-corrected feature signals are used. The equivalent LLD thresholds shown are thus the sums of background signal and (3×average b-SD).

Figure 10:
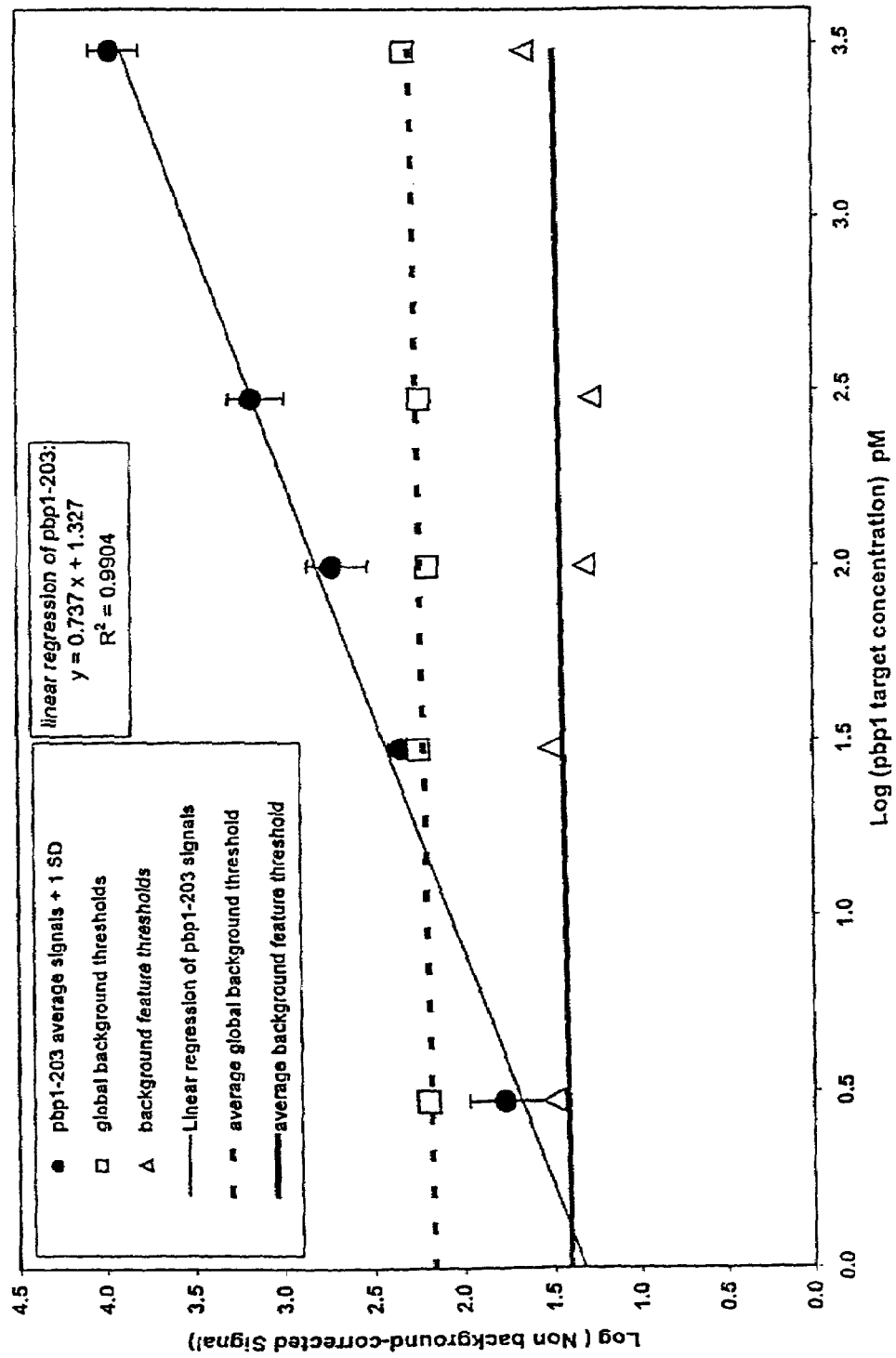
FIG. 10 uses the non-background-corrected signal data the pbp1-203 probe (SEQ ID NO:35) from the five arrays described in FIG. 7. The global background and average background feature thresholds from each array are also shown. The use background features, as opposed to global background, yields a much lower LLD, i.e. increased sensitivity.

As explained above, the global background method uses the minimum of all local background signals (signal=35, from Table 7 for the 30 pM target array) as the estimated background signal for all features on that array and uses three times the SD among the local backgrounds (e.g. 3×b-SD signal=369, from Table 7 for the 30 pM target array) as the noise component for that array. The threshold value (3×average b-SD) for the five xenotitration arrays is 138. Since non-background-corrected data is used in FIG. 12, the global background threshold plotted for each array is the sum of (the global background signal of that array+138). The average of these five sums is the threshold used to calculate the LLD, shown as the "average global background threshold" line in FIG. 10. The LLD calculated for the pbp1-203 probe (SEQ ID NO:35) using the global background method is 16.7 pM.

As explained above, the background feature method uses the average of all background features of an array as the estimated background signal for all features on that array (e.g. signal=20, from Table 7 for the 30 pM target array). The background features 3×interfeature_SD is calculated (e.g. 3×b-SD signal=24, from Table 7 for the 30 pM target array) as the noise component for that array. The threshold value (3×average b-SD) for the five xenotitration arrays is 15. Since non-background-corrected data is used in FIG. 10, the background feature threshold plotted for each array is the sum of (the average background feature signal of that array+15). The average of these five sums is the threshold used to calculate the LLD, shown as the "average background feature threshold" line in FIG. 12. The LLD calculated for the pbp1-203 probe (SEQ ID NO:35) using the background feature method is 0.9 pM, 18-fold lower than that calculated with the global background method.

Figure 11:
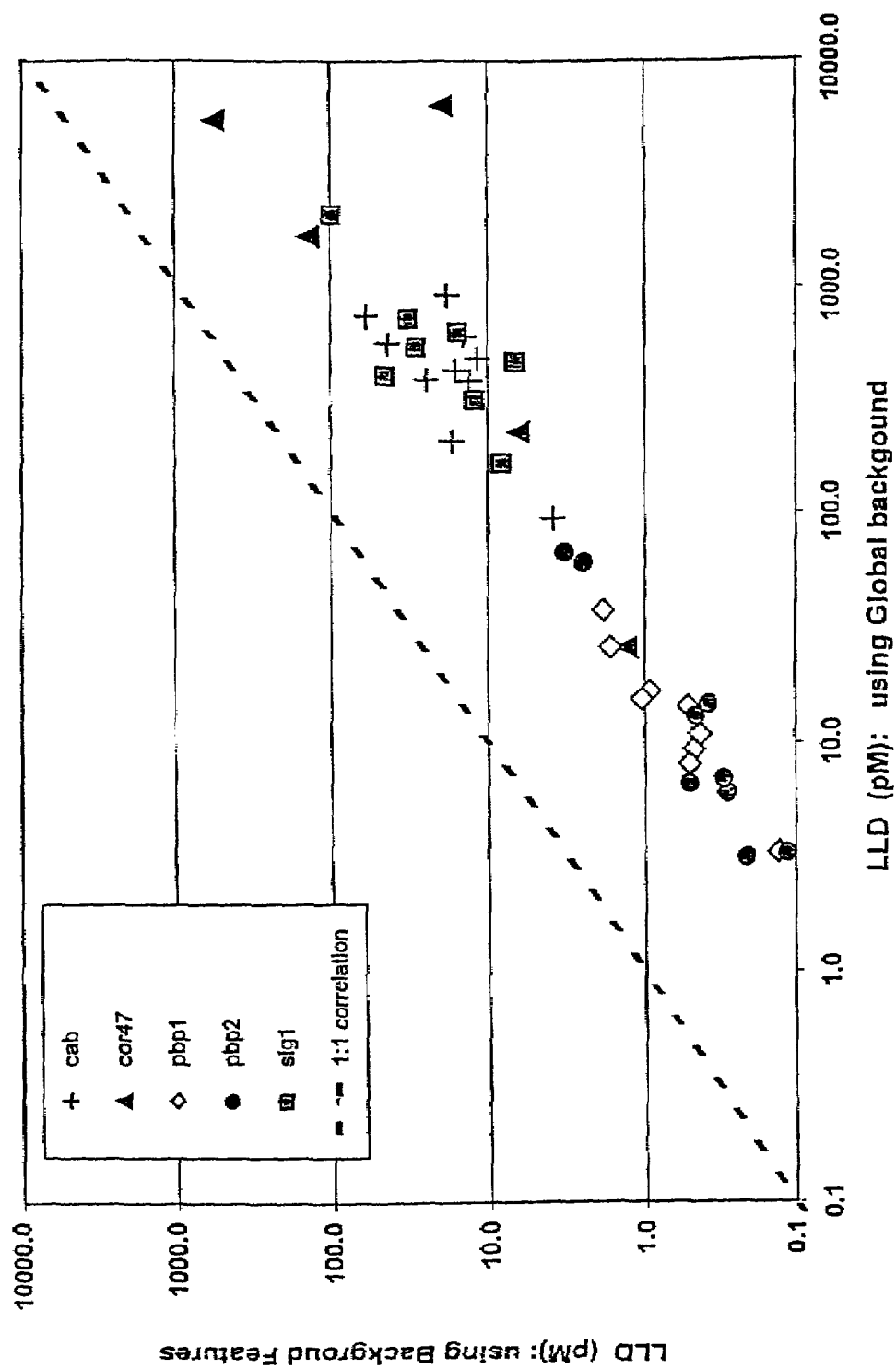
FIG. 11 illustrates the effect of the method of background correction has on LLD calculations, wherein the use background features, as opposed to global background, yields a much lower LLD, i.e. increased sensitivity. The data was obtained from the five arrays described in FIG. 7.

LLD values were calculated with both background-correction methods for all of the xenogene probes studied in the xenotitration experiment. FIG. 11 shows a plot comparing the LLD's calculated with global background vs. background features. The data includes 42 probes, each having 3 to 4 features replicates per array, that were hybridized with five concentrations of their specific targets (i.e. 3 pM to 3,000 pM). It is clear from FIG. 11 that the use of background features for background signal estimation and threshold determination yields much lower limits of detection than the use of global background (i.e LLD values below the 1:1 correlation line). The average decrease in LLD from using global background to using background features is 30-fold, a very large increase in assay sensitivity.

EXAMPLE 8

Identification of Background Features Suitable for 60-Mer Arrays

A series of probes were designed using the initial structure of "ProST1". ProST 1 is a 16-mer hairpin designed and validated originally with in-situ array composed of 25-mer experimental probes. The ProST1 structure was extended to varying lengths with sequences of varying AT/GC content. The intra-molecular binding delta G was estimated for these probes using the program available the web site having an address made up of http:// placed before and .cgi placed after: bioinfo.math.rpi.edu/~mfold/dnalform1

The probe name, sequence, sequence length, and delta G of these proposed negative controls are shown in Table 10. One of the designs utilized three hairpins in the same probe structure ("3×SLv1"). A series of short probes were also designed to determine their effectiveness of correcting background. Since the short probes are linear, not hairpin sequences, their delta G values were not calculated.

TABLE 10

| Name | Probe Sequence (5' to 3') | Seq ID NO: | Length | Delta G |
|---|---|---|---|---|
| ProST1 | GCTAGCGAAAGCTAGC | 36 | 16 | -3.1 |
| GD1 | GCTAGCGCGCGCGCGCGCGCGCGCGCGCGAAAGCGCGCGCGCGCGCGCGCGCGCGCGCTAGC | 37 | 60 | -38.5 |
| GD2 | GCTAGCTAGCTAGCTAGCTAGC | 38 | 22 | |
| GD3 | GCTAGCTAGCTAGCTAGCTAGCTAGCGCGAAAGCTAGCTAGCTAGCTAGCTAGCTAGCGC | 39 | 60 | -18.3 |
| GD5 | GCTAGCGAAAGCTAGC | 40 | 16 | |
| GD6 | GCTAGC | 41 | 6 | |
| GD8 | GCTAGCTAGCTAGCTAGCTAGCGCTAGCGAAAGCTAGCGCTAGCTAGCTAGCTAGCTAGC | 42 | 60 | -23.2 |
| GD9 | TTTTTTTT | 43 | 8 | |
| GD10 | GCTAGCTAGCTAGCTAGC | 44 | 18 | |
| GO11 | GCTAGCTAGCTAGCTAGCGCTAGCGAAAGCTAGCGCTAGCTAGCTAGCTAGCTTTTTTTT | 45 | 60 | -20.0 |
| GD12 | GCTAGCTAGCTAGCGCTAGCGAAAGCTAGCGCTAGCTAGCTAGC | 46 | 44 | -16.4 |
| GD13 | GCTAGCTAGCGCTAGCGAAAGCTAGCGCTAGCTAGCTTTTTTTT | 47 | 44 | -13.2 |
| GD14 | GCTAGCTAGCGCTAGCGAAAGCTAGCGCTAGCTAGC | 48 | 36 | -13.1 |
| GD15 | GCTAGCGCTAGCGAAAGCTAGCGCTAGCTTTTTTTT | 49 | 36 | -9.9 |
| GD16 | CTAGCGCTAGCGAAAGCTAGCGCTA | 50 | 25 | -7.9 |
| GD17 | GCTAGCGAAAGCTAGCTTTTTTTTT | 51 | 25 | -3.3 |
| GD18 | GCGCGCTAGCGAAAGCTAGCGCGC | 52 | 24 | -9.5 |
| 3xSLv1 | GCTAGCGAAAGCTAGCTTTTCGATCGGAAACGATCGTTTTCCAGTGACGAAAGTCACTGG | 53 | 60 | -11.9 |

An Agilent in-situ array was designed with the above probes present in replicate (~N=8 probes per sequence/ per array). The arrays also had 60-mer probes present that were designed against the human RefSeq database. The arrays were hybridized with K562 RNA target labeled with both Cy3 (green channel) and Cy5 (red channel). Since this is a "self-self" experiment, a plot of background corrected red versus green signal should yield a straight line.

The data for the 60-mer experimental probes (N=969 genes, 4 replicate features) were background corrected by subtracting the average signal of the ProST1 probes, for each signal channel. FIG. 12 shows that this data is not linear, but rather curves downwards at the low end. This is diagnostic of incorrect background correction; specifically, under-correcting green in relation to red signal.

Figure 13:
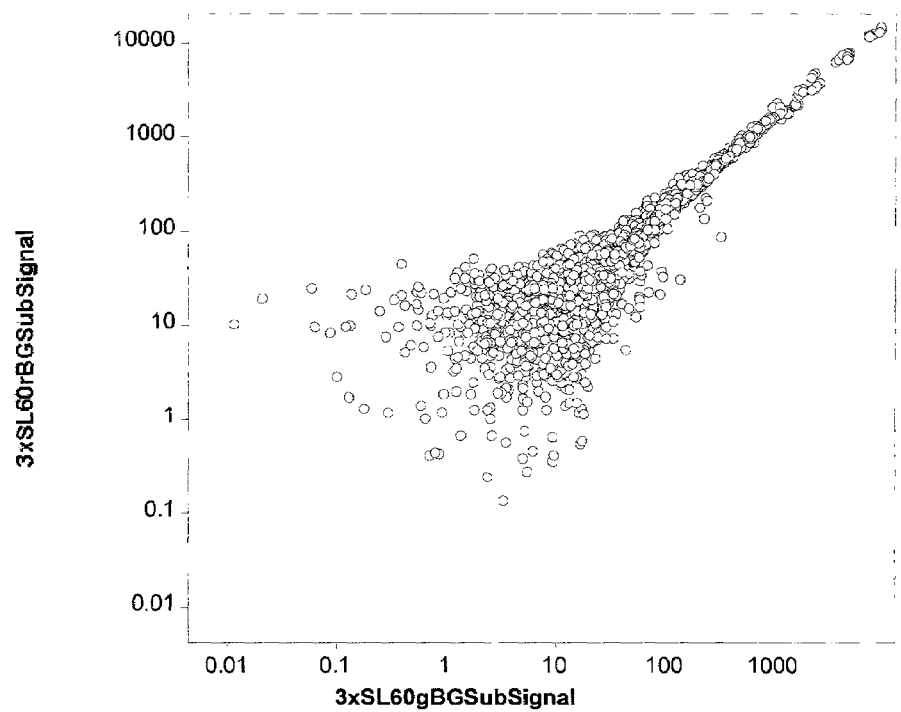
FIGS. 13 and 14 provide a graphical representation of the results obtained from a two-color self-self hybridization using the background features 3XSLv1 or GD1, respectively.
Figure 14:
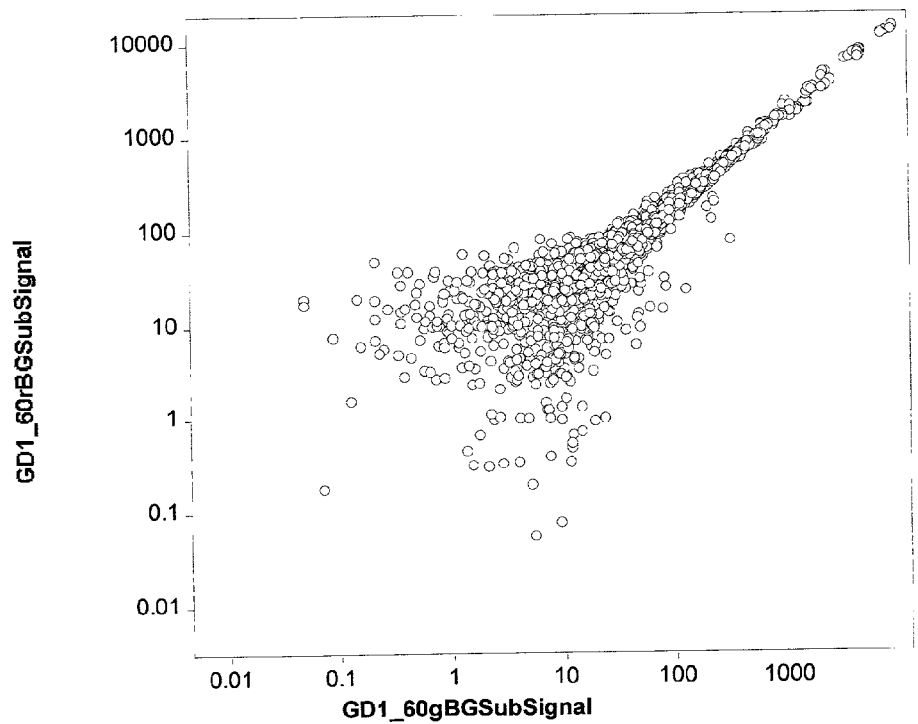

The experimental features were also background corrected using each of the above proposed negative controls. FIGS. 13 and 14 show the data using 3XSLv1 or GD1, respectively, as the negative controls. Both of these probes, as well as the other 60-mer negative controls, yield much more linear background corrected red versus green plots. At the low signal end, where there is more noise in the correlation, the noise is seen to be symmetrical about the correlation line, now. Thus, the 16-mer ProST1 did not estimate the background signal of the 60-mer experimental probes as well as the 60-mer negative controls. The average signal of the 60-mer negative controls was higher than the 16-mer ST1 and reflected the green versus red background more accurately.

Figure 15:
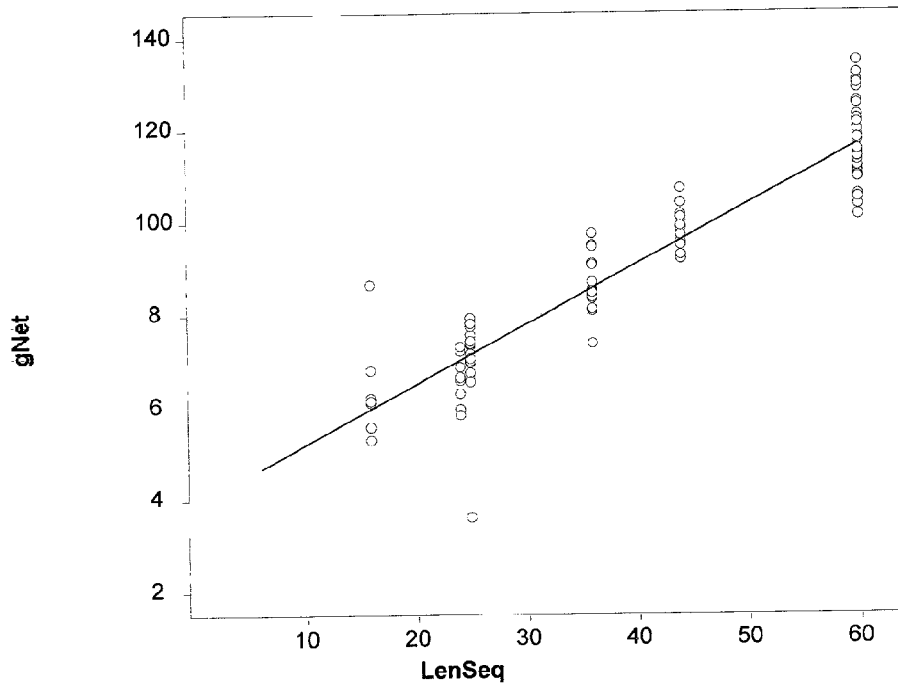
FIG. 15 provides a graphical representation of the relation between the background signal detected by the negative controls versus their sequence length.

The relation between the background signal detected by the negative controls versus their sequence length is shown in FIG. 15. All lengths of hairpin probes were used for this plot. There is a positive linear correlation ($R^2$=0.935); that is, the longer the probe, the more background signal is seen. This is consistent with the hypothesis that non-specific binding of targets by array-bound probes increases as the probe length increases.

The above correlation protocol can be used to correct experimental probes of varying lengths on the same array. That is, by using multiple negative probe sequences spanning the range of lengths of experimental probes (e.g., from 25-mers to 60-mers), one can fit a linear regression function and correct 25-mers, 45-mers, 60-mers, etc by using the calculated expected background signal (for that channel) for that length of probe. The data from FIG. 15 yields the following fit:

Expected green background signal=39+1.29×(Probe_Length)

It is evident from the above results and discussion that the subject invention provided substantial advantages in nucleic acid hybridization assays. The background features of the subject arrays provide for an extremely accurate approximation of the true background of the array, making results more reliable. In addition, the subject invention provides readily practice methods useful for identifying background features for any type of array, including oligonucleotide, polynucleotide and even cDNA arrays. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

What is claimed is:

1. A method of detecting the presence of an analyte nucleic acid in a sample, said method comprising:
   (a) providing a nucleic acid array comprising:
      (i) at least one hybridization feature to which said analyte nucleic acid specifically binds under stringent hybridization conditions; and
      (ii) at least one background feature, wherein said background feature is a polymeric composition that comprises background probes that do not hybridize to complementary nucleic acids in said sample; (b) contacting said nucleic acid array with said sample under stringent hybridization conditions;
   (c) washing said nucleic acid array;
   (d) detecting a hybridization signal from said hybridization feature and background signal from said background feature;
   (e) subtracting said background signal from said hybridization signal to obtain a background corrected hybridization signal; and
   (f) relating said background corrected hybridization signal to the presence of said analyte target nucleic acid in said sample to detect the presence of said analyte target nucleic acid in said sample;
   wherein said method is further characterized by including a target nucleic acid labeling step prior to said detecting step (d).

2. The method according to claim 1, wherein said labeling step comprises labeling any analyte target nucleic acids present in said sample with a member of a signal producing system prior to said contacting step (b).

3. The method according to claim 1, wherein said labeling step comprises labeling any analyte target nucleic acids present on said array following step(b) with a member of a signal producing system.

4. The method according to claim 1, wherein said background feature provides a background signal following said contacting step that comprises: (a) a feature substrate background component; (b) a probe background component; and (c) a non-specific binding background component.

5. The method according to claim 4, wherein said background probes of said background feature range in length from about 5 to about 100 nt.

6. The method according to claim 4, wherein said background probes are selected from the group consisting of empirically observed inactive probes, probes forming intramolecular structures, short probes, probes comprising reverse polarity nucleotide analogs, probes comprising abasic phosphodiesters or probes comprising modified nucleotidic units.

7. The method according to claim 1, wherein said background feature provides a signal that is the same as a signal generated by a validated background feature made up of empirically observed inactive probes.

8. The method according to claim 7, wherein said validated background feature is made up of nucleic acids having a nucleic acid sequence selected from the group consisting of SEQ ID NOS: 05 to 18, 24 to 32 and 36 to 53.

9. The method according to claim 1, wherein said background feature tests positive in a two-color self-self array hybridization assay.

10. A method of detecting the presence of an analyte nucleic acid in a sample, said method comprising:

(a) providing a nucleic acid array comprising;
  (i) at least one hybridization feature to which said analyte nucleic acid specifically binds under stringent hybridization conditions; and
  (ii) at least one background feature, wherein said background feature is a polymeric composition that comprises background probes that do not hybridize to complementary nucleic acids in said sample; (b) contacting said nucleic acid array with said sample under stringent hybridization conditions;
(c) washing said nucleic acid array;
(d) detecting a hybridization signal from said hybridization feature and background signal from said background feature;
(e) subtracting said background signal from said hybridization signal to obtain a background corrected hybridization signal; and
(f) relating said background corrected hybridization signal to the presence of said analyte target nucleic said in said sample to detect the presence of said analyte target nucleic acid in said sample;
wherein said method is further characterized by including a target nucleic acid labeling step prior to said detecting step (d); and
further wherein said background feature provides a background signal following said contacting step that comprises: (i) a feature substrate background component; (ii) a probe background component; and (iii) a non-specific binding background component and tests positive in a two-color self-self array hybridization assay.

11. The method according to claim 10, wherein said labeling step comprises labeling any analyte target nucleic acids present in said sample with a member of a signal producing system prior to said contacting step (b).

12. The method according to claim 10, wherein said labeling step comprises labeling any analyte target nucleic acids present on said array following step(b) with a member of a signal producing system.

13. The method according to claim 12, wherein said background probes of said background feature range in length from about 6 to about 100 nt.

14. The method according to claim 10, wherein said background probes are selected from the group consisting of empirically observed inactive probes, probes forming intramolecular structures, short probes, probes comprising reverse polarity nucleotide analogs, probes comprising abasic phosphodiesters or probes comprising modified nucleotidic units.

15. The method according to claim 10, wherein said background feature provides a signal that is the same as a signal generated by a validated background feature made up of empirically observed inactive probes.

16. The method according to claim 15, wherein said validated background feature is made up of nucleic acids having a nucleic acid sequence selected from the group consisting of SEQ ID NOS: 05 to 18, 24 to 32 and 36 to 53.

* * * * *

UNITED STATES PATENT AND TRADEMARK OFFICE
CERTIFICATE OF CORRECTION

| | | |
|---|---|---|
| PATENT NO. | : 7,078,167 B2 | Page 1 of 1 |
| APPLICATION NO. | : 09/899381 | |
| DATED | : July 18, 2006 | |
| INVENTOR(S) | : Delenstarr et al. | |

It is certified that error appears in the above-identified patent and that said Letters Patent is hereby corrected as shown below:

Column 66, line 12, in Claim 13, delete "6" and insert -- 5 --, therefor.

Signed and Sealed this

Twelfth Day of December, 2006

JON W. DUDAS
*Director of the United States Patent and Trademark Office*